United States Patent
Bromidge et al.

(10) Patent No.: US 6,423,717 B1
(45) Date of Patent: Jul. 23, 2002

(54) SULPHONAMIDE DERIVATIVES, PROCESS FOR THEIR PREPARATION, AND THEIR USE AS MEDICAMENTS

(75) Inventors: Steven Mark Bromidge, Sawbridgeworth; Francis David King, Bishops Stortford; Paul Adrian Wyman, Epping, all of (GB)

(73) Assignee: SmithKline Beecham p.l.c., Brentford (GB)

(*) Notice: Subject to any disclaimer, the term of this patent is extended or adjusted under 35 U.S.C. 154(b) by 0 days.

(21) Appl. No.: 09/643,200

(22) Filed: Aug. 21, 2000

Related U.S. Application Data

(63) Continuation of application No. 09/331,378, filed as application No. PCT/EP97/07159 on Dec. 15, 1997, now abandoned.

(30) Foreign Application Priority Data

| Dec. 19, 1996 | (GB) | 9626377 |
| Jan. 17, 1997 | (GB) | 9700901 |
| Oct. 27, 1997 | (GB) | 9722757 |

(51) Int. Cl.[7] ............ A61K 31/496; C07D 295/135; C07D 403/12; C07D 409/12; C07D 409/14
(52) U.S. Cl. ............ 514/252.13; 514/253.06; 514/254.03; 514/254.09; 514/254.11; 514/253.11; 514/254.04; 514/255.03; 514/324; 514/336; 514/414; 514/422; 514/443; 544/363; 544/364; 544/367; 544/368; 544/373; 544/376; 544/379; 544/394; 544/395; 546/202; 546/281.1; 548/400; 548/454; 549/55
(58) Field of Search ............... 544/363, 368, 544/373, 376; 514/253.06, 254.11, 252.13, 254.03, 254.09

(56) References Cited

U.S. PATENT DOCUMENTS

| 4,315,014 A | 2/1982 | Mich et al. | |
| 5,932,599 A | 8/1999 | Bos et al. | 514/352 |
| 5,939,451 A | 8/1999 | Bos et al. | 514/415 |
| 6,030,976 A | 2/2000 | Bos et al. | 514/275 |

FOREIGN PATENT DOCUMENTS

| DE | 081861 | 1/1998 |
| EP | 021 580 A | 1/1981 |
| EP | 0 076 072 A | 4/1983 |
| EP | 0 558 999 A | 9/1993 |
| EP | 0 609 734 A | 8/1994 |
| EP | 0 533 267 A | 3/1995 |
| JP | 04330057 | * 11/1992 |
| WO | WO 87 03782 A | 7/1987 |
| WO | WO 90 09787 A | 9/1990 |
| WO | WO 95 06637 A | 3/1995 |
| WO | WO 95 11243 A | 4/1995 |
| WO | WO 95 15954 A | 6/1995 |
| WO | WO 95 32967 A | 12/1995 |

OTHER PUBLICATIONS

Hidake et al., Chemical Abstracts, vol. 119, No. 139132, Abstract for JP 04330057 (Nov. 18, 1992), 1993.*
Saxena, Pharmac. Ther., vol. 66, pp. 339–368, (1995).*
Sayo, et al., Chem. and Pharm. Bull. vol. 25, No. 4, pp. 640–646, 1997.

* cited by examiner

*Primary Examiner*—Emily Bernhardt
(74) *Attorney, Agent, or Firm*—Soma G. Simon; Mary E. McCarthy; Charles M. Kinzig

(57) ABSTRACT

Novel sulphonamide derivatives having CNS activity, processes for their preparation and their use as medicaments are disclosed. The present compounds are of formula (I) or a salt thereof:

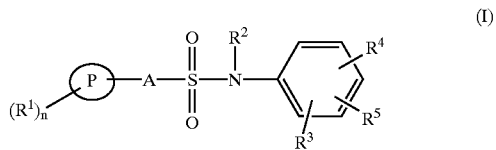

(I)

wherein:
P is benzothiophene, benzothiadiazole, quinoline, benzofuran or indole;

A is a single bond, a $C_{1-6}$alkylene or a $C_{1-6}$alkenylene group;

$R^1$ is halogen, $C_{1-6}$alkyl optionally substituted by one or more halogen atoms, $C_{3-6}$cycloalkyl, $COC_{1-6}$alkyl, $C_{1-6}$alkoxy, $OCF_3$, hydroxy, hydroxy$C_{1-6}$alkyl, hydroxy$C_{1-6}$alkoxy, $C_{1-6}$alkoxy$C_{1-6}$alkoxy, nitro, amino, $C_{1-6}$alkylamino or $C_{1-6}$dialkylamino, cyano or $R^1$ is phenyl or naphthyl;

n is 0, 1, 2, 3, 4, 5, or 6;

$R^2$ is hydrogen, $C_{1-6}$alkyl or aryl $C_{1-6}$alkyl or $R^2$ is linked to $R^3$ to form a group $(CH_2)_2$ or $(CH_2)_3$;

$R^3$ is a group $R^5$ or together with $R^5$ forms a group $(CH_2)_2O$ or $(CH_2)_3O$ or $R^3$ is linked to $R^2$ to form a group $(CH_2)_2$ or $(CH_2)_3$;

$R^4$ is an N-piperazine ring optionally substituted by $C_{1-6}$alkyl; and $R^5$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, nitro, trifluoromethyl, cyano or aryl.

13 Claims, No Drawings

SULPHONAMIDE DERIVATIVES, PROCESS FOR THEIR PREPARATION, AND THEIR USE AS MEDICAMENTS

This application is a continuation of Ser. No. 09/331,378 filed Jun. 18, 1999, now abandoned, which is a 371 of international application PCT/EP97/07159 filed Dec. 15, 1997.

This invention relates to compounds having pharmacological activity, processes for their preparation, to compositions containing them and to their use in the treatment of CNS disorders.

EPA 0 021 580 and EPA 0 076 072 describe sulphonamide derivatives which are disclosed as having antiarrhythmic activity. A structurally distinct class of compounds has now been discovered, which have been found to have $5HT_6$ receptor antagonist activity. $5HT_6$ receptor antagonists are believed to be of potential use in to the treatment of certain CNS disorders such as anxiety, depression, epilepsy, obsessive compulsive disorders, migraine, cognitive memory enhancement e.g. for the treatment Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI (gastrointestinal) disorders such as IBS (Irritable Bowel Syndrome).

The present invention therefore provides, in a first aspect, a compound of formula (I) or a salt thereof:

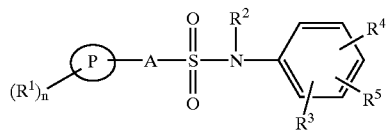

wherein:
P is phenyl, naphthyl, a bicyclic heterocyclic ring or is a 5 to 7-membered heterocyclic ring each containing 1 to 4 heteroatoms selected from oxygen, nitrogen or sulphur;
A is a single bond, a $C_{1-6}$alkylene or a $C_{1-6}$alkenylene group;
$R^1$ is halogen, $C_{1-6}$alkyl optionally substituted by one or more halogen atoms, $C_{3-6}$cycloalkyl, $COC_{1-6}$alkyl, $C_{1-6}$alkoxy, $OCF_3$, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, nitro, amino, $C_{1-6}$alkylamino or di$C_{1-6}$alkylamino, cyano or $R^1$ is phenyl, naphthyl, a bicyclic heterocyclic ring or is a 5 to 7-membered heterocyclic ring each containing 1 to 4 heteroatoms selected from oxygen, nitrogen or sulphur;
n is 0, 1, 2, 3, 4, 5 or 6,
$R^2$ is hydrogen, $C_{1-6}$ alkyl or aryl $C_{1-6}$ alkyl;
$R^3$ is a group $R^5$ or together with $R^5$ forms a group $(CH_2)_2O$ or $(CH_2)_3O$ or $R^3$ is linked to $R^2$ to form a group $(CH_2)_2$ or $(CH_2)_3$;
$R^4$ is —X(CH$_2$)p—$R^6$ where X is a single bond, CH$_2$, O, NH or N— $C_{1-6}$ alkyl and p is 0 to 6 and $R^6$ is an optionally substituted 5- to 7-membered heterocyclic ring containing 1 to 3 heteroatoms selected from nitrogen, sulphur or oxygen, or $R^6$ is $NR^7R^8$ where $R^7$ and $R^8$ are independently hydrogen, $C_{1-6}$ alkyl or aryl $C_{1-6}$ alkyl; and $R^5$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, $C_{1-6}$alkanoyl, nitro, trifluoromethyl, cyano or aryl.

$C_{1-6}$ Alkyl groups, whether alone or as part of another group, may be straight chain or branched. Preferred alkyl groups are generally methyl and ethyl. As used herein the term aryl includes optionally substituted phenyl and naphthyl.

When P is a bicyclic heterocyclic ring suitable examples include benzothiophene, quinoline or isoquinoline. When P is a 5 to 7-membered heterocyclic ring suitable examples include thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl, pyrrolidinyl and pyrazinyl. The heterocyclic rings can be linked to the remainder of the molecule via any suitable carbon atom or, when present, a nitrogen atom. Suitable substituents for these rings include $R^5$ groups as defined above.

Preferably P is phenyl, thiophene, benzothiophene or naphthyl.

Preferably A is a single bond, an ethylene group or a —CH═CH— group. Most preferably A is a single bond.

When $R^1$ is a heterocyclic group suitable examples include those listed above. Preferably $R^1$ is halogen or $C_{1-6}$alkyl optionally substituted by one or more halogen atoms, for example methyl or trifluoromethyl.

Preferably n is 0, 1, 2 or 3, particularly 1 or 2.

Suitably $R^2$ is hydrogen or $C_{1-6}$alkyl. Preferably $R^2$ is hydrogen.

It will be appreciated that when $R^3/R^5$ groups are linked together the two groups must be attached to adjacent carbon atoms of the phenyl ring. Preferably $R^3$ is a group $R^5$, in particular hydrogen.

Preferably $R^4$ is meta with respect to the sulphonamide linkage. Preferably X is a bond, p is 0 and $R^6$ is an optionally substituted 5- to 7-membered heterocyclic ring. The heterocyclic rings can be linked to the remainder of the molecule via a carbon atom or, when present, a nitrogen atom. Optional substituents for these rings, which can be present on carbon and/or nitrogen atoms, include $C_{1-6}$alkyl, in particular methyl. More preferably $R^4$ is N-piperazine optionally substituted by $C_{1-6}$alkyl, particularly unsubstituted piperazine.

Preferably $R^5$ is $C_{1-6}$alkoxy, most preferably methoxy. Preferably $R^5$ is para with respect to the sulphonamide linkage.

A preferred meaning for P-A is benzo[b]thiophen-2-yl or benzo[b]thiophen-3-yl optionally substituted by one or two $R^1$ groups, especially 5-chloro-3-methyl-benzo[2]thiophen-2-yl.

Particular compounds of the invention include: 4-Bromo-N-[4-methoxy-3-(4-methylpiperazin-1-yl)phenyl]benzenesulfonamide, N-[4-Methoxy-3-(4-methylpiperazin-1-yl)phenyl]-2-thiophenesulfonamide, N-[4-Methoxy-3-(4-methylpiperazin-1-yl)phenyl]-5-(pyridin-2-yl)-2-thiophenesulfonamide, 2,5-Dichloro-N-[4-methoxy-3-(4-methylpiperazin-1-yl)phenyl]-3-thiophenesulfonamide, 4-Bromo-5-chloro-N-[4-methoxy-3-(4-methylpiperazin-1-yl)phenyl]-2-thiophenesulfonamide, N-[4-Methoxy-3-(4-methylpiperazin-1-yl)phenyl]benzenesulfonamide, 3-Bromo-5-chloro-N-[4-methoxy-3-(4-methylpiperazin-1-yl)phenyl]-2-thiophenesulfonamide, N-[4-Methoxy-3-(4-methylpiperazin-1-yl)phenyl]benzylsulfonamide, 2-Bromo-N-[4-methoxy-3-(4-methylpiperazin-1-yl)phenyl]benzenesulfonamide, 3-Bromo-N-[4-methoxy-3-(4-methylpiperazin-1-yl)phenyl]benzenesulfonamide, 3-Chloro-N-[4-methoxy-3-(4-methylpiperazin-1-yl)phenyl]-4-methylbenzenesulfonamide, N-[4-Methoxy-3-(4-methylpiperazin-1-yl)phenyl]-trans-styrenesulfonamide, 3,4-Dichloro-N-[4-methoxy-3-(4-methylpiperazin-1-yl)phenyl]benzenesulfonamide, 3,5-Dichloro-N-[4-methoxy-3-(4-methylpiperazin-1-yl)phenyl]benzenesulfonamide, N-[4-Methoxy-3-(4-methylpiperazin-1-yl)phenyl]-[2,1,3]benzothiadiazole-4-sulfonamide, 5-Chloro-N-[4-methoxy-3-(4-methylpiperazin-1-yl)phenyl]-3-methyl-2-benzothiophenesulfonamide, N-[4-Methoxy-3-(4-methylpiperazin-1-yl)phenyl]-2-methyl-5-nitrobenzenesulfonamide, N-[4-Methoxy-3-(4-methylpiperazin-1-yl)phenyl]-2-trifluoromethylbenzenesulfonamide, N-[4-Methoxy-3-(4-methylpiperazin-1-yl)phenyl]-3-trifluoromethylbenzenesulfonamide, 2,5-Dimethoxy-N-[4-methoxy-3-(4-methylpiperazin-1-yl)phenyl]benzenesulfonamide, 4-Fluoro-N-[4-methoxy-3-(4-methylpiperazin-1-yl)phenyl]benzenesulfonamide, 4-Chloro-N-[4-methoxy-3-(4-methylpiperazin-1-yl)phenyl]benzenesulfonamide, 4-Iodo-N-[4-methoxy-3-(4-methylpiperazin-1-yl)phenyl]benzenesulfonamide, 4-Ethyl-N-[4-methoxy-3-(4-methylpiperazin-1-yl)phenyl]benzenesulfonamide, 4-tert-Butyl-N-[4-methoxy-3-(4-methylpiperazin-1-yl)phenyl]benzenesulfonamide, 4-Isopropyl-N-[4-methoxy-3-(4-methylpiperazin-1-yl)phenyl]benzenesulfonamide, 4-tert-Amyl-N-[4-methoxy-3-(4-methylpiperazin-1-yl)phenyl]benzenesulfonamide, N-[4-Methoxy-3-(4-methylpiperazin-1-yl)phenyl]-4-trifluoromethoxybenzenesulfonamide, 4-n-Butoxy-N-[4-methoxy-3-(4-methylpiperazin-1-yl)phenyl]benzenesulfonamide, N-[4-Methoxy-3-(4-methylpiperazin-1-yl)phenyl]-4-methylbenzenesulfonamide, 5-Chloro-N-[4-methoxy-3-(4-methylpiperazin-1-yl)phenyl]-2-thiophenesulfonamide, N-[4-Methoxy-3-(4-methylpiperazin-1-yl)phenyl]-1-naphthalenesulfonamide, N-[4-Methoxy-3-(4-methylpiperazin-1-yl)phenyl]-2-naphthalenesulfonamide, 5-(Dimethylamino)-N-[4-methoxy-3-(4-methylpiperazin-1-yl)phenyl]-1-naphthalenesulfonamide, 4-Bromo-N-[7-(4-methylpiperazin-1-yl)-2,3-dihydrobenzofuran-5-yl]benzenesulfonamide, 4-Methoxy-N-[4-methoxy-3-(4-methypiperazin-1-yl)phenyl]benzenesulfonamide, 4-n-Butyl-N-[4-methoxy-3-(4-methylpiperazin-1-yl)phenyl]benzenesulfonamide, 4-Amino-N-[4-methoxy-3-(4-methylpiperazin-1-yl)phenyl]benzenesulfonamide, 2-Chloro-N-[4-methoxy-3-(4-methylpiperazin-1-yl)phenyl]benzenesulfonamide, 3-Chloro-N-[4-methoxy-3-(4-methylpiperazin-1-yl)phenyl]benzenesulfonamide, 2,3,4-Trichloro-N-[4-methoxy-3-(4-methylpiperazin-1-yl)phenyl]benzenesulfonamide, 4-Chloro-N-[4-methoxy-3-(4-methylpiperazin-1-yl)phenyl]-2,5-dimethylbenzenesulfonamide, N-[4-Methoxy-3-(4-methylpiperazin-1-yl)phenyl]-3-methylbenzenesulfonamide, 2,5-Dibromo-3,6-difluoro-N-[4-methoxy-3-(4-methylpiperazin-1-yl)phenyl]benzenesulfonamide, N-[4-Methoxy-3-(4-methylpiperazin-1-yl)phenyl]-2,3,5,6-tetramethylbenzenesulfonamide, 5-Chloro-2-methoxy-N-[4-methoxy-3-(4-methylpiperazin-1-yl)phenyl]benzenesulfonamide, 3-Fluoro-N-[4-methoxy-3-(4-methylpiperazin-1-yl)phenyl]benzenesulfonamide, 3,4-Difluoro-N-[4-methoxy-3-(4-methylpiperazin-1-yl)phenyl]benzenesulfonamide, 4-Chloro-N-[4-methoxy-3-(4-methylpiperazin-1-yl)phenyl]-3-nitrobenzenesulfonamide, 3-Chloro-N-[4-methoxy-3-(4-methylpiperazin-1-yl)phenyl]-2-methylbenzenesulfonamide, N-[4-Methoxy-3-(4-methylpiperazin-1-yl)phenyl]-8-quinolinesulfonamide, N-[4-Methoxy-3-(4-methylpiperazin-1-yl)phenyl]-4-phenylbenzenesulfonamide, 3,4-Dimethoxy-N-[4-methoxy-3-(4-methylpiperazin-1-yl)phenyl]benzenesulfonamide, N-[4-Methoxy-3-(4-methylpiperazin-1-yl)phenyl]-3,5-dimethyl-4-isoxazolesulfonamide, 4-Bromo-N-[4-methoxy-3-(4-ethylpiperazin-1-yl)phenyl]benzenesulfonamide, 2,3-Dichloro-N-[4-methoxy-3-(4-methylpiperazin-1-yl)phenyl]-benzenesulfonamide, 5-Iodo-N-[4-methoxy-3-(4-methylpiperazin-1-yl)phenyl]-2-methylbenzenesulfonamide, 3-Iodo-N-[4-methoxy-3-(4-methylpiperazin-1-yl)phenyl]benzenesulfonamide, 3-Iodo-N-[4-methoxy-3-(4-methylpiperazin-1-yl)phenyl]-4-methylbenzenesulfonanide, 5-Chloronaphthalene-2-sulfonic acid [4-methoxy-3-(4-methylpiperazin-1-yl)phenyl]amide, 5-Chloronaphthalene-1-sulfonic acid [4-methoxy-3-(4-methylpiperazin-1-yl)phenyl]amide, 4-Chloronaphthalene-1-sulfonic acid [4-methoxy-3-(4-methylpiperazin-1-yl)phenyl]amide, 7-Chloronaphthalene-1-sulfonic acid [4-methoxy-3-(4-methylpiperazin-1-yl)phenyl]amide, 5-Chloro-2-methylbenzo[b]thiophene-3-sulfonic acid [4-methoxy-3-(4-methylpiperazin-1-yl)phenyl]amide, Benzofuran-2-sulfonic acid [4-methoxy-3-(4-methylpiperazin-1-yl)phenyl]amide, 1-Methyl-1H-indole-2-sulfonic acid [4-methoxy-3-(4-methylpiperazin-1-yl)phenyl]amide, 5-Pyridin-2-ylthiophene-2-sulfonic acid (4-methoxy-3-piperazin-1-ylphenyl)amide, N-(4-Methoxy-3-piperazin-1-ylphenyl)-3-trifluoromethylbenzenesulfonamide, 3-Iodo-N-(4-methoxy-3-piperazin-1-ylphenyl)benzenesulfonamide, 3,5-Dimethylisoxazole-4-sulfonic acid (4-methoxy-3-piperazin-1-ylphenyl)amide, 3,5-Dichloro-N-(4-methoxy-3-piperazin-1-ylphenyl)benzenesulfonamide, 2,5-Dibromo-3,6-difluoro-N-(4-methoxy-3-piperazin-1-ylphenyl)benzenesulfonamide, Naphthalene-1-sulfonic acid (4-methoxy-3-piperazin-1-ylphenyl)amide, 2-Bromo-5-chlorothiophene-2-sulfonic acid (4-methoxy-3-piperazin-1-ylphenyl)amide, 2-Chloro-4-fluoro-N-(4-methoxy-3-piperazin-1-ylphenyl)benzenesulfonamide, 3-Bromo-N-(4-methoxy-3-piperazin-1-ylphenyl)benzenesulfonamide, 3-Chloro-N-(4-methoxy-3-piperazin-1-ylphenyl)benzenesulfonamide, 5-Chloronaphthalene-2-sulfonic acid (4-methoxy-3-piperazin-1-ylphenyl)amide, 4-Bromo-5-chlorothiophene-2-sulfonic acid (4-methoxy-3-piperazin-1-ylphenyl)amide, 2,5-Dichlorothiophene-3-sulfonic acid (4-methoxy-3-piperazin-1-ylphenyl)amide 4-Bromo-N-(4-methoxy-3-piperazin-1-ylphenyl)benzenesulfonamide, 5-Chloro-3-methylbenzo[b]thiophene-2-sulfonic acid (4-methoxy-3-piperazin-1-ylphenyl)amide, 5-Chloro-2-methylbenzo[b]thiophene-3-sulfonic acid (4-methoxy-3-piperazin-1-ylphenyl)amide, 1-Methyl-1H-indole-2-sulfonic acid (4-methoxy-3-piperazin-1-ylphenyl)amide, Benzofuran-2-sulfonic acid (4-methoxy-3-piperazin-1-ylphenyl)amide, Naphthalene-2-sulfonic acid(4-methoxy-3-piperazin-1-ylphenyl)amide, 5-Chloronaphthalene-1-sulfonic acid(4-methoxy-3-piperazin-1-ylphenyl)amide, 4-Chloro-2,5-dimethyl-N-(4-methoxy-3-piperazin-1-ylphenyl)benzenesulfonamide, 3,4-Dichloro-N-(4-methoxy-3-piperazin-1-ylphenyl)benzenesulfonamide, 3-Chloro-N-(4-methoxy-3-piperazin-1-ylphenyl)-4-methylbenzenesulfonamide, 2-Trifluoromethyl-N-(4-methoxy-3-piperazin-1-ylphenyl)benzenesulfonamide, 4-Iodo-N-(4-methoxy-3-piperazin-1-ylphenyl)benzenesulfonamide, 4-tert-Butyl-N-(4-methoxy-3-piperazin-1-ylphenyl)benzenesulfonamide, Naphthalene-1-sulfonic acid [7-(4-methylpiperazin-1-yl)-2,3-dihydrobenzofuran-5-yl]amide, Thiophene-2-sulfonic acid [7-(4-methylpiperazin-1-yl)-2,3-dihydrobenzofuran-5-yl]amide, 5-Chlorothiophene-2- sulfonic acid [7-(4-methylpiperazin-1-yl)-2,3-dihydrobenzofuran-5-yl]amide, 5-Pyridin-2-ylthiophene-2-sulfonic acid [7-(4-methylpiperazin-1-yl)-2,3-dihydrobenzofuran-5-yl]amide, 2,5-Dichlorothiophene-3-sulfonic acid [7-(4-methylpiperazin-1-yl)-2,3-dihydrobenzofuran-5-yl]amide, 4-Bromo-5-chlorothiophene-2-sulfonic acid [7-(4-methylpiperazin-1-yl)-2,3-dihydrobenzofuran-5-yl]amide, 3-Bromo-5-chlorothiophene-2-sulfonic acid [7-(4-methylpiperazin-1-yl)-2,3-dihydrobenzofuran-5-yl]amide, 4-Chloro-2,5-dimethyl-N-[7-(4-methylpiperazin-1-yl)-2,3-dihydrobenzofuran-5-yl]benzenesulfonamide, 5-Chloro-3-methylbenzo[b]thiophene-2-sulfonic acid [7-(4-methylpiperazin-1-yl)-2,3-dihydrobenzofuran-5-yl]amide, Naphthalene-2-sulfonic acid [7-(4-methylpiperazin-1-yl)-2,3-dihydrobenzofuran-5-yl]amide. 3-Bromo-N-[7-(4-methylpiperazin-1-yl)-2,3-dihydrobenzofuran-5-yl]benzenesulfonamide, 3,5-Dichloro-N-[7-(4-methylpiperazin-1-yl)-2,3-dihydrobenzofuran-5-yl]benzenesulfonamide, 4-tert-Butyl-N-[7-(4-methylpiperazin-1-yl)-2,3-dihydrobenzofuran-5-yl]benzenesulfonamide, 2,5-Dibromo-3,6-difluoro-N-[7-(4-methylpiperazin-1-yl)-2,3-dihydrobenzofuran-5-yl]benzenesulfonamide, 2,5-Dibromo-3,6-difluoro-N-(7-piperazin-1-yl-2,3-dihydrobenzofuran-5-yl)benzenesulfonamide, 4-Chloro-2,5-dimethyl-N-(7-piperazin-1-yl-2,3-dihydrobenzofuran-5-yl)benzenesulfonamide, 5-Chloro-3-methyl benzo[b]thiophene-2-sulphonic acid [3-(4-cyclopropylmethylpiperazin-1-yl)-4-methoxy-phenyl]amide, 5-Chloro-3-methyl benzo [b]thiophene-2-sulphonic acid [3-(4-benzyl-piperazin-1-yl)-4-methoxy-phenyl]-amide, 5-Chloro-3-methyl-benzo[b]thiophene-2-sulphonic acid [4-hydroxy-3-(4-methylpiperazin-1-yl)-phenyl]-amide, 5-Chloro-3-methyl-benzo[b]thiophene-2-sulphonic acid [4-benzyloxy-3-(4-methylpiperazin-1-yl)-phenyl]-amide, 5-Chloro-3-methyl-benzo[b]thiophene-2-sulphonic acid [4-ethoxy-3-(4-methylpiperazin-1-yl)-phenyl]-amide, 5-Chloro-3-methyl-benzo[b]thiophene-2-sulphonic acid [4-isopropoxy-3-(4-methylpiperazin-1-yl)-phenyl]-amide, 5-Chloro-3-methyl-benzo[b]thiophene-2-sulphonic acid [4-methoxy-3-(1-methylpyrrolidin-3-yloxy)-phenyl]-amide, Naphthalene-2-sulfonic acid [2-bromo-5-(4-methylpiperazin-1-yl)phenyl]amide 5-Chloro-3-methylbenzo[b]thiophene-2-sulfonic acid [4-chloro-3-(4-methylpiperazin-1-yl)phenyl]amide, Naphthalene-2-sulfonic acid [4-bromo-3-(4-methylpiperazin-1-yl)phenyl]amide, 5-Chloro-3-methylbenzo[b]thiophene-2-sulfonic acid[3-(2-dimethylaminoethoxy)-4-iodophenyl]amide, 5-Chloro-3-methylbenzo[b]thiophene-2-sulfonic acid [1-(2-dimethylaminoethyl)-2,3-dihydro-1H-indol-6-yl]amide, 1-(5-Chloro-3-methylbenzo[b]thiophene-2-sulfonyl)-6-(4-methylpiperazin-1-yl)-2,3-dihydro-1H-indole, 1-(5-Chloro-3-methylbenzo[b]thiophene-2-sulfonyl)-5-methoxy-6-(4-methylpiperazin-1-yl)-2,3-dihydro-1H-indole 5-Chloro-3-methylbenzo[b]thiophene-2-sulfonic acid[4-methoxy-2-methyl-3-(4-methylpiperazin-1-yl)phenyl]amide, 5-Chloro-3-methylbenzo[b]thiophene-2-sulfonic acid[2-(2-hydroxyethyl)-4-methoxy-3-(4-methylpiperazin-1-yl)phenyl]amide, 1-(5-Chloro-3-methylbenzo[b]thiophene-2-sulfonyl)-5-methoxy-4-(4-methylpiperazin-1-yl)-2,3-dihydro-1H-indole hydrochloride, 5-Chloro-3-methylbenzo[b]thiophene-2-sulfonic acid[3-methoxy-4-(4-methylpiperazin-1-yl)phenyl]amide, 4-Bromo-N-[4-methoxy-3-(1-methyl-1,2,3,6-tetrahydropyridin-4-yl)phenyl]benzenesulfonamide, 5-Chloro-3-methylbenzo[b]thiophene-2-sulfonic acid [4-methoxy-3-(1-methyl-1,2,3,6-tetrahydropyridin-4-yl)phenyl]amide 5-Chloro-3-methylbenzo[b]thiophene-2-sulfonic acid [4-methoxy-3-(1-methylpiperidin-4-yl)phenyl]amide Naphthalene-2-sulfonic acid [3-(4-methylpiperazin-1-yl)phenyl]amide and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic.

Compounds of formula (I) may also form solvates such as hydrates, and the invention also extends to these forms. When referred to herein, it is understood that the term 'compound of formula (I)' also includes these forms.

Certain compounds of formula (I) are capable of existing in stereoisomeric forms including diastereomers and enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises the coupling of a compound of formula (II):

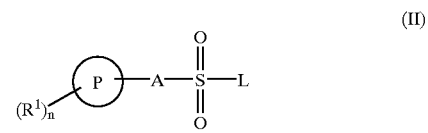

(II)

in which $R^1$, n, P, and A are as defined in formula (I) or protected derivatives thereof and L is a leaving group with a compound of formula (III):

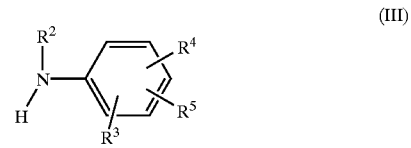

(III)

in which $R^2$, $R^3$, $R^4$ and $R^5$ are as defined in formula (I) or protected derivatives thereof and optionally thereafter:
  removing any protecting groups,
  forming a pharmaceutically acceptable salt.

Suitable leaving groups include halogen, in particular chloro. The reaction of a compounds of formulae (II) and (III) is carried out by mixing the two reagents together, optionally in an inert solvent such as acetone. Such a reaction may be carried out in the presence of base.

Those skilled in the art will appreciate that it may be necessary to protect certain groups. Suitable protecting groups and methods for their attachment and removal are conventional in the art of organic chemistry, such as those described in Greene T. W. 'Protective groups in organic synthesis' New York, Wiley (1981). For example, suitable protecting groups for the piperazine group include BOC, $COCCl_3$, $COCF_3$ and methyl the latter of which may be removed by treatment with 1-chloroethyl chloroformate according to standard procedures.

N-substituted piperazines can be prepared by acylation or alkylation of the appropriate NH-piperazine compound according to standard procedures.

Compounds of formulae (II) and (III) are commercially available or may be prepared according to known methods or analogous to known methods.

Pharmaceutically acceptable salts may be prepared conventionally by reaction with the appropriate acid or acid derivative.

Compounds of formula (I) and their pharmaceutically acceptable salts have $5HT_6$ receptor antagonist activity and are believed to be of potential use in the treatment of certain CNS disorders such as anxiety, depression, epilepsy, obsessive compulsive disorders, migraine, Alzheimers disease (cognitive memory enhancement), sleep disorders (including disturbances of Circadian Rythym), feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

DESCRIPTION 1

1-(2-Metboxy-5-nitrophenyl)piperazine (D1)

A solution of 5M sulphuric acid (114 ml) was added over 0.3 h to 1-(2-methoxyphenyl)piperazine (110 g) at 0° C. with stirring. To the ice-cooled stirred slurry was then added, over 1.75 h, concentrated sulphuric acid (560 ml) and the temperature was maintained for a further 1.5 h. Potassium nitrate (71.5 g) was then added portionwise over 1.5 h to the stirred, cold, viscous mixture which was then left to stand for 18 h. The solution was poured onto ice (2 Kg) and the resulting cooled mixture brought to pH 12 by the addition of 40% sodium hydroxide solution. The oily mixture was extracted with ethyl acetate (2×2L) and the combined organic extracts were washed with water (3L), dried ($Na_2SO_4$), concentrated to a residue which was stirred with diethyl ether (700 ml) to give the title compound (D1) as a yellow solid, m.p. 84–87° C. (95 g, 70%). $MH^+238$.

DESCRIPTION 2

4-tert-Butoxyearbonyl-1-(2-methoxy-5-nitrophenyl) piperazine (D2)

To a stirred heterogeneous solution of 1-(2-methoxy-5-nitrophenyl)piperazine (D1) (99.2 g) in tetrahydrofuran (1.1L) and water (1.1L) was added a solution of di-tert-butyldicarbonate (91.3 g) in tetrahydrofuran (300 ml) over 0.5 h. Potassium carbonate (60.7 g) was then added in portions over 0.5 h and the mixture was stirred at ambient temperature for 18 h. The whole was concentrated to remove the organic solvent and the resulting mixture was extracted with dichloromethane (2×1L). The combined organic phases were washed with water (1L), dried ($Na_2SO_4$) and concentrated to a residue which was stirred with diethyl ether (500 ml) and hexane (750 ml) to afford the title compound (D2) as a yellow solid, m.p. 136–7°°C. (125 g, 89%). $MH^+338$.

DESCRIPTION 3

4-tert-Butoxycarbonyl-1-(5amino-2-methoxyphenyl) piperazine (D3)

A slurry of 10% palladium on carbon (10 g) in a solution of 4-tert-butoxycarbonyl-1-(2-methoxy-5-nitrophenyl)

piperazine (D2) (124.5 g) in ethanol (3.5L) and water (50 ml) was stirred with hydrogen at ambient temperature and atmospheric pressure for 18 h. The reaction mixture was filtered and the filtrate concentrated to afford the title compound (D3) as a gum (112 g, 99%). MH$^+$308.

DESCRIPTION 4–14

General Preparation of N-[4-Methoxy-3-(4-t-butoxycarbonyl-1-piperazinyl)phenyl] Arylsulfonamides (D4–D14)

A solution of 4-t-butoxycarbonyl-1-(5-amino-2-methoxyphenyl)piperazine (D3) (15.6 mmol), diisopropylethylamine (15.6 mmol) and the appropriate aryl sulfonyl chloride (15.6 mmol) in dichloromethane (100 ml) was stirred at room temperature for 18 h. The mixture was concentrated and the residue chromatographed on silica gel eluting with a dichloromethane/methanol gradient to give the following pure title products.

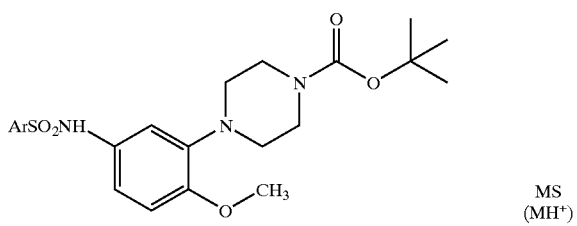

| | MS (MH$^+$) |
|---|---|
| 2-Chloro-4-fluoro-N-[4-methoxy-3-(4-t-butoxycarbonyl-1-piperazinyl)phenyl]benzenesulfonamide (D4) | * |
| 3-Bromo-N-[4-methoxy-3-(4-t-butoxycarbonyl-1-piperazinyl)phenyl]benzenesulfonamide (D5) | * |
| 3-Chloro-N-[4-methoxy-3-(4-t-butoxycarbonyl-1-piperazinyl)phenyl]benzenesulfonamide (D6) | * |
| 4-Bromo-5-chlorothiophene-2-sulfonic acid [4-methoxy-3-(4-t-butoxycarbonyl-1-piperazinyl)phenyl] amide (D7) | * |
| 2,5-Dichlorothiophene-3-sulfonic acid [4-methoxy-3-(4-t-butoxycarbonyl-1-piperazinyl)phenyl] amide (D8) | * |
| 4-Bromo-N-[4-methoxy-3-(4-t-butoxycarbonyl-1-piperazinyl)phenyl]benzenesulfonamide (D9) | 526/528 |
| 5-Chloro-3-methylbenzo[b]thiophene-2-sulfonic acid [4-methoxy-3-(4-t-butoxycarbonyl-1-piperazinyl)phenyl] amide (D10) | 552/554 |
| 5-Chloro-2-methylbenzo[b]thiophene-3-sulfonic acid [4-methoxy-3-(4-t-butoxycarbonyl-1-piperazinyl)phenyl] amide (D11) | 552/554 |
| Benzofuran-2-sulfonic acid [4-methoxy-3-(4-t-butoxycarbonyl-1-piperazinyl)phenyl] amide (D12) | 488 |
| 1-Methyl-1H-indole-2-sulfonic acid [4-methoxy-3-(4-t-butoxycarbonyl-1-piperazinyl)phenyl] amide (D13) | 501 |
| 5-Chloronaphthalene-2-sulfonic acid (4-methoxy-3-(4-t-butoxycarbonyl-1-piperazinyl)phenyl] amide (D14) | * |

*Intermediate used crude without isolation

DESCRIPTION 10

5-Chloro-3-methylbenzo[b]thiophene-2-sulfonic Acid (4-Methoxy-3-(4-tert-butoxycarbonylpiperazin-1-ylphenyl)amide (D10)

Pyridine (60 ml) was added to a stirred solution of 4-tert-butoxycarbonyl-1-(5-amino-2-methoxyphenyl) piperazine (D3) (112 g) in dichloromethane (1L) at ambient temperature under argon. To this solution was added over 0.75 h a solution of 5-Chloro-3-methylbenzo[b]thiophene-2-sulfonyl chloride (102.5 g) in dichloromethane (2.1L) and the purple solution was stirred for 18 h. The mixture was then washed with 1M hydrochloric acid solution (3L), water (3L), dried (Na$_2$SO$_4$), and concentrated to a foam which was stirred with acetone (800 ml) and water (800 ml) to afford the title compound (D10) as a maroon solid, m.p. 100–103° C. (194.9 g, 97%). MH$^+$ 552/554.

DESCRIPTION 15

1-(2-Methoxy-5-nitrophenyl)-4-trichloroacetylpiperazine (D15)

A solution of 5-nitro-1-(2-methoxyphenyl)piperazine (D1) (44 g) in dichloromethane (300 ml) was added to a stirred solution of trichloroacetylchloride (32 ml) in dichloromethane (200 ml) over 0.25 h. After 3 hrs, the reaction mixture was concentrated and the residue recrystallised from chloroform to yield the title compound (D15) as a yellow solid (43 g, 61%). Found MH$^+$ 382/384.

DESCRIPTION 16

1-(5Amino-2-methoxyphenyl)-4-trichloroacetylpiperazine (D16)

A solution of stannous chloride dihydrate (27 g) in concentrated HCl (60 ml) was slowly added to a stirred suspension of 1-(2-methoxy-5-nitrophenyl)-4-trichloroacetylpiperazine (D15) (15 g) in concentrated HCl/ ethanol (1:2, 120 ml). After 24 hrs, the mixture was filtered, diluted with dichloromethane (600 ml) and basified with Na$_2$CO$_3$ solution. The layers were separated, the organic phase dried, concentrated to ⅓ the volume and acidified with 1M ethereal HCl solution to afford the title compound (D16) as a green solid (2.5 g, 15%). Found MH$^+$ 352.

DESCRIPTION 17

Cyclopropyl-[4-(2-methoxy-5-nitrophenyl)-piperazin-1-yl]methanone (D17)

To a solution of 1-(2-methoxy-5-nitrophenyl)-piperazine (500 mg, 2.1 mmol) in dichloromethane (50 ml) at 0° C. under argon was added triethylamine (0.59 ml, 4.2 mmol) and cyclopropane carbonyl chloride (2.1 mmol). Stirring was continued for 12 hrs. The reaction mixture was concentrated in vacuo and partitioned between saturated aqueous NaHCO$_3$ and dichloromethane. The organic layer was dried over sodium sulphate and concentrated in vacuo to give the title compound (D17) in 90% yield. Found MH$^+$ 306.

DESCRIPTION 18

[4-(2-Methoxy-5-nitrophenyl)-piperazin-1-yl]phenyl methanone (D18)

The title compound was prepared in 85% yield using the procedure outlined in D17 using benzoyl chloride. Found MH$^+$ 342.

DESCRIPTION 19

[4-(5-Amino-2-methoxy-phenyl)-piperazin-1-yl] cyclopropyl methanone (D19)

A solution of the cyclopropyl-[4-(2-methoxy-5-nitrophenyl)-piperazin-1-yl]methanone (D17) (1.8 mmol) in ethanol was hydrogenated over 10% Palladium on charcoal catalyst for 2 hrs at room temperature to give the title compound in 91% yield. Found MH$^+$ 276.

DESCRIPTION 20

[4-(5-Amino-2-methoxy-phenyl)-piperazin-1-yl Phenyl Methanone (D20)

The title compound was prepared in 95% yield using the procedure outlined in D19. Found MH$^+$ 312

DESCRIPTION 21

3-(4-Cyclopropylmethyl-piperazin-1-yl)-4-methoxy-phenylamine (D21)

To a solution of [4-(5-amino-2-methoxy-phenyl)-piperazin-1-yl]cyclopropyl methanone (D19) (1.6 mmol) in dry THF (10 ml) under argon was added LiAlH$_4$ (240 mg, 6.4 mmol). The resulting mixture was heated to reflux for 12 hrs and cooled before quenching with water (0.25 ml), 10% aqueous NaOH (0.25 ml) and finally water (0.75 ml). Filtration through celite and concentration in vacuo afforded the title compound (D21) in 75% yield. Found MH$^+$ 262.

DESCRIPTION 22

3-(4Benzyl-piperazin-1-yl)-4-methoxy-phenylamine (D22)

The title compound was prepared in 76% yield using the procedure outlined in D21. Found MH$^+$ 298.

DESCRIPTION 23

Methane Sulphonic Acid 1-Methyl Pyrrolidin-3-yl Ester (D23)

To a solution of 1-methyl-pyrrolidin-3-ol (2.0 g, 20 mmol) and triethylamine (3 ml, 22 mmol) in dichloromethane (25 ml) at 0° C. under argon was added methane sulphonyl chloride (2.4 g, 21 mmol). Stirring was continued at 0° C. to room temperature for 1 hr before partitioning between saturated aqueous sodium bicarbonate and dichloromethane. The organic phase was dried over sodium sulphate and concentrated in vacuo to afford the crude mesylate (3.6 g) which was used directly in the next step.

DESCRIPTION 24

3-(2-Methoxy-5-nitro-phenoxy)-1-methyl-pyrrolidine (D24)

A solution of 2-methoxy-5-nitro phenol (5.1 g, 30 mmol) in DMF (10 ml) was added to sodium hydride (1.6 g, 66 mmol) under argon. After 1 hr a solution of the crude mesylate (D23, 3.6 g, 20 mmol) in DMF (10 ml) was added and the reaction mixture warmed to 50° C. for 48 hrs. The reaction was cooled, quenched with water and concentrated in vacuo before partitioning between saturated aqueous sodium bicarbonate and dichloromethane. The organic phase was dried over sodium sulphate and concentrated in vacuo. The residue was purified by chromatography on silica gel to afford the title compound (D24). Found MH$^+$ 253.

DESCRIPTION 25

4-Methoxy-3-(1-methyl-pyrrolidin-3-yloxy)phenylamine (D25)

A solution of 3-(2-methoxy-5-nitro-phenoxy)-1-methyl-pyrrolidine (3.0 g, 0.12 mmol) in ethanol (50 ml) was hydrogenated over 10% palladium on charcoal catalyst for 2 hrs to afford the title compound (D25). Found MH$^+$ 223.

DESCRIPTION 26

1-(4-Bromo-3-nitrophenyl)-4-methylpiperazine (D26)

A solution of 1-methyl-4-(3-nitrophenyl)piperazine (EP0533267A) (1.0 g; 4.5 mmol) in glacial acetic acid (25 ml) was treated with bromine (0.23 ml; 1 equivalent). The reaction mixture was stirred at 75° overnight, then cooled, filtered, and the yellow sticky solid was partitioned between potassium carbonate (aq) and 2% methanol in dichloromethane. The organic phase was dried (Na$_2$SO$_4$) and evaporated under reduced pressure to leave the title compound (D26) as a viscous orange oil (928 mg, 68%) MH$^+$=300/302.

DESCRIPTION 27

2-Bromo-5-(4-methylpiperazin-1-yl)phenylamine (D27)

A suspension of iron powder (1.77 g, 31.6 mmol) in saturated aqueous ammonium chloride solution (140 ml) at 100° C., was treated dropwise with a solution of 1-(4-bromo-3-nitrophenyl)-4-methylpiperazine (D26) (3.54 g, 11.8 mmol) in methanol (70 ml). The mixture was refluxed for a further 1 h, and was then cooled and partitioned between water and 3% methanol in dichloromethane. The organic phase was dried (Na$_2$SO$_4$) and evaporated under reduced pressure to give the crude product. This was purified by chromatography on silica gel, eluting with methanol and dichloromethane to give the title compound (D27) as a white solid (2.18 g, 68%) MH$^+$=270/272.

DESCRIPTION 28

2-Methoxy-6-methyl)phenylamine (D28)

A solution of 1-methoxy-3-methyl-2-nitrobenzene (15.04 g, 0.09 mol) in ethanol (250 ml) was hydrogenated over 10% palladium on charcoal (4 g) at atmospheric pressure and at room temperature, for 18 h. The catalyst was removed by filtration, and the filtrate evaporated under reduced pressure to leave the title compound (D28) as an amber oil, which crystallised on standing (11.18 g, 91%). $^1$H NMR (250 MHz, CDCl$_3$) δ (ppm): 6.75–6.65 (m, 3H), 3.81 (s, 3H), 3.72 (br s, 2H), 2.19 (s, 3H).

DESCRIPTION 29

1-(2-Metboxy-6methyl)phenyl)-4-methylpiperazine (D29)

A mixture of 2-methoxy-6-methyl)phenylamine (D28) (3.62 g, 26.4 mmol), mechlorethamine hydrochloride (12.7 g, 66 mmol) and potassium carbonate (15 g) in chlorobenzene (90 ml) was refluxed under argon for 20 h. The mixture was cooled and filtered, and the filtrate evaporated under reduced pressure to leave the title compound (D29) as a red oil which slowly crystallised on standing (5.4 g, 93%) MH$^{30}$=221.

DESCRIPTION 30

1-(6-Methoxy-2-methyl-3-nitrophenyl)-4-methylpiperazine (D30)

A solution of 1-(2-methoxy-6-methylphenyl)-4-methylpiperazine (D29) (6.2 g, 28 mmol) in concentrated sulfuric acid (50 ml) was treated portionwise with potassium nitrate (3.3 g, 33 mmol) over 5 mins, maintaining the temperature at 25–30° C. The mixture was stirred overnight at room temperature, then added to ice, and basified with 40% sodium hydroxide solution. The mixture was extracted with dichloromethane and the organic phase was dried (Na$_2$SO$_4$) and evaporated under reduced pressure to give crude compound. Purification by chromatography on silica

DESCRIPTION 31

2-[3-Methoxy-2-(4-methylpiperazin-1-yl)-6-nitrophenyl]ethanol (D31)

A mixture of 1-(6-methoxy-2-methyl-3-nitrophenyl)-4-methylpiperazine (D30) (360 mg, 1.36 mmol), dry dimethylsulfoxide (3 ml), paraformaldehyde (82 mg, 2.72 mmol) and potassium tert-butoxide (52 mg, 0.46 mmol) was heated at 70–75° C. for 30 h. After cooling, the mixture was partitioned between water and ethyl acetate. The organic phase was dried ($Na_2SO_4$) evaporated under reduced pressure and purified by chromatography on silica gel, eluting with methanol and dichloromethane, to give the title compound (D31) as a yellow solid (152 mg, 38%) $MH^+$=296.

DESCRIPTION 32

2-[6-Amino-3-methoxy-2-(4-methylpiperazin-1-yl)phenyl]ethanol (D32)

The title compound (D32) was prepared from 2-[3-methoxy-2-(4-methylpiperazin-1-yl)-6-nitrophenyl]ethanol (D31) (142 mg, 0.48 mmol) using the method of Description 28 as a clear oil which crystallised on standing (94 mg, 74%) $MH^+$=266.

DESCRIPTION 33

4-Methoxy-2-methyl-3-(4-methylpiperazin-1-yl)phenylamine (D33)

The title compound (D33) was prepared from 1-(6-methoxy-2-methyl-3-nitrophenyl)-4-methylpiperazine (D30) (150 mg, 0.56 mmol) using the method of Description 28 as a tan powder (78 mg, 59%) $MH^+$=236.

DESCRIPTION 34

1-(2-Methoxy-4-nitrophenyl)-4-methylpiperazine (D34)

A mixture of N-methylpiperazine (216 mg, 2.15 mmol), 2-bromo-5-nitroanisole (1 g, 4.3 mmol), potassium carbonate (447 mg, 3.23 mmol), copper (I) bromide (86.6 mg, 0.30 mmol) in pyridine (0.5 ml) and toluene (2 ml) was heated at 100° C. overnight. After cooling, the mixture was partitioned between water and ether and the aqueous phase was further extracted with ethyl acetate. The combined organic phases were dried ($Na_2SO_4$) and evaporated under reduced pressure, to give the crude product. This was purified by chromatography on silica gel, eluting with methanol and dichloromethane, to give the title compound (D34) as a yellow/brown oil (80 mg, 15%) $MH^+$=252.

DESCRIPTION 35

3-Methoxy-4-(4-methylpiperazin-1-yl)phenylamine (D35)

The title compound (D35) was prepared from 1-(2-methoxy-4-nitrophenyl)-4-methylpiperazine (D34) (80 mg, 0.319 mmol) using the method of Description 28 (50 mg, 71%) $MH^+$=222.

DESCRIPTION 36

4-(2-Methoxy-5-nitrophenyl)pyridine (D36)

A stirred mixture of 2-bromo-4-nitroanisole (7.6 g, 32.7 mmol), 4-pyridineboronic acid (4.07 g, 33 mmol) and powdered sodium carbonate (13.8 g, 5 equivalents) in 1:1 1,2-dimethoxyethane: water (1,360 ml) was degassed for 0.5 hr, by the passage of a stream of argon. Tetrakistriphenylphosphine palladium (0) (1.35 g) was added, and the mixture was cooled, the solvents evaporated under reduced pressure to approximately half-volume, and the aqueous residue was acidified with 5N hydrochloric acid and washed with ethyl acetate. The acid phase was then basified with solid potassium carbonate, and extracted into ethyl acetate, the organic phase was dried ($Na_2SO_4$) and evaporated under reduced pressure to give the title compound (D36) as a pale yellow solid (3.4 g, 45%).

$^1$H NMR (250 MHz, $CDCl_3$) δ (ppm): 8.7 (d, 2H), 8.32 (d, 1H), 8.29–8.25 (m, 1H), 7.47 (d, 2H), 7.09 (d, 1H), 3.96 (s, 3H).

DESCRIPTION 37

4-(2-Methoxy-5-nitrophenyl)-1-methyl-1,2,3,6tetrahydropyridine (D37)

A solution of 4-(2-methoxy-5-nitrophenyl)pyridine (D36) (3.4 g, 14.8 mmol) in acetone (150 ml) was treated with excess iodomethane (5 ml) and the mixture stirred at room temperature overnight. The precipitated quaternary salt was filtered off, washed with acetone and dried, giving 5.02 g. This was dissolved in 1:1 ethanol: water (230 ml) and treated portionwise at room temperature, under argon, with sodium borohydride (1.23 g, 32.4 mmol). The mixture was stirred for 1 h at room temperature then potassium carbonate (10 g) was added and the organic layer was separated from the aqueous phase, which was back-extracted with ethyl acetate. The organic phases were combined and dried ($Na_2SO_4$) and evaporated under reduced pressure to give the title compound (D37) as an orange oil, which slowly crystallised (3.05 g, 91%).

$^1$H NMR (250 MHz, $CDCl_3$) δ (ppm): 8.15 (d, 1H), 8.05 (s, 1H), 6.9 (d, 1H), 5.9–5.84 (m, 1H), 3.9 (s, 3H), 3.15–3.05 (m, 2H), 2.7–2.61 (m, 2H), 2.6–2.5 (m, 2H), 2.4 (s, 3H).

DESCRIPTION 38

4-Methoxy-3-(1-methylpiperidin-1-yl)phenylamine (D38)

A solution of 4-(2-methoxy-5-nitrophenyl)-1-methyl-1,2,3,6-tetrahydropyridine (D37) (1.0 g, 4 mmol) in ethanol (50 ml) and glacial acetic acid (5 ml) was hydrogenated over 10% palladium on charcoal at 50° C. and 50 psi for 4 days. The catalyst was removed by filtration, the filtrate evaporated under reduced pressure and the residue partitioned between potassium carbonate (aq) and dichloromethane. The organic phase was dried ($Na_2SO_4$) and evaporated under reduced pressure to give the title compound (D38) as a brown oil which rapidly crystallised to a light tan powder (760 mg, 86%). $MH^+$=221.

DESCRIPTION 39

4-Methoxy-3-(1-methyl-1,2,3,6-tetrahydropyridin-4-yl)phenylamine Hydrochloride (D39)

A solution of 4-(2-methoxy-5-nitrophenyl)-1-methyl-1,2,3,6-tetrahydropyridine (D37) (570 mg, 2 mmol), in ethanol (35 ml), was warmed to 60° C. and treated dropwise with a solution of stannous chloride (2 g) in conc. hydrochloric acid (4 ml). The mixture was heated for a further 2 h after addition, and allowed to cool. The precipitate was filtered off, and washed with ethanol to give the title compound (D39) as a pale yellow powder (580 mg, 99%). $MH^+$=219.

gel eluting with methanol and dichloromethane afforded the title compound (D30) (4.56 g, 61%) $MH^+$=266.

General Preparation of Aryl-N(4-methoxy-3-piperazin-1-yl)-benzenesulfonamide Hydrochlorides on Solid Phase

DESCRIPTION 40

Preparation of 1-(2-Methoxy-5-nitrophenyl) piperazin-4yl Bound to Merrifield Resin A solution of 1-(2-methoxy-5-nitrophenyl)piperazine (9.7 g) in N-methylpyrrolidin-2-one (NMP)) (150 ml) was heated with chloromethylpolystyrene-divinylbenzene resin (Merrifield, 150–300 mesh) at 60° C. for 24 h under argon. The resin was then filtered, washed (NMP; dichloromethane/methanol gradient) and dried to give the title compound (6.9 g) which was used directly in Description 41.

DESCRIPTION 41

Preparation of 1-(5-Amino-2-methoxyphenyl) piperazin-4-yl Bound to Merrifield Resin A solution of stannous chloride dihydrate (9 g) in N,N-dimethylformamide (DMF) (120 ml) was stirred for 72 h at room temperature under argon with the resin from Description 40 (6.9 g). The resin was filtered, washed (DMF; dichloromethane/methanol gradient) and dried to give the title compound (6.6 g) which was used directly in Description 42.

DESCRIPTION 42

General Preparation of Aryl-N-(4-methoxy-3-(4-polymerylpiperazin-1-yl)-benzenesulfonamide Bound to Merrifield Resin A solution of aryl sulfonyl chloride (0.4 mmol) and di-isopropylethylamine (1 mmol) in dichloromethane (3 ml) was agitated for 24 h at room temperature with the resin (0.1 mmol) from Description 41. The resin was then filtered, washed (dichloromethane; dichloromethane/methanol gradient; methanol) to yield the title compound which was used directly in Examples 133–137.

DESCRIPTION 43

(S)-1-Methyl-2-(2-methoxy-5-nitrophenoxy)-pyrrolidine (D43)

A solution of 2-methoxy-5-nitrophenol (5.58 g; 0.033 mol), (S)-1-methyl-2-hydroxymethylpyrrolidine (3.45 g; 0.03 mol) and triphenylphosphine (8.65 g; 0.033 mol) in dry THF (80 ml) was cooled to 50 and treated with DEAD (5.2 ml; 0.033 mol) over 15 min. The reaction mixture was allowed to stand at RT for 16 h, then evaporated in vacuo and partitioned 5% NaOH(aq)/Et2O. The organic phase was separated and extracted with 10% HCl(aq). The aqueous extract was washed with Et2O, basified with 40% NaOH(aq) and extracted with Et2O. The organic extracts were washed with H2O, dried over Na2SO4 and evaporated in vacuo to yield the title compound (D43) (6.79 g; 85%) MH$^+$=267.

DESCRIPTION 44

(S)-1-Methyl-2-(2-methoxy-5-aminophenoxy) pyrrolidine (D44)

A solution of (S)-1-methyl-2-(2-methoxy-5-nitrophenoxy)pyrrolidine (D43) (6.79 g; 0.0255 mol) in ethanol (200 ml) was hydrogenated in the presence of 5% Pd/C catalyst (0.5 g added as an aqueous slurry) at atmospheric pressure and RT for 16 hours. The catalyst was removed by filtration through kieselguhr and the filtrate evaporated in vacuo to yield the title compound (D44) (5.64 g; 93%) MH$^+$=237.

EXAMPLE 1

N-[4-Methoxy-3-(4-methyl-1-piperazinyl)phenyl] thiophene2-ylsulfonamide

A solution of thiophene-2-sulfonyl chloride (82 mg; 0.45 mmol) in acetone (2 ml) was added to a solution of 4-methoxy-3-(4-methylpiperazin-1-yl)aniline (100 mg; 0.45 mmol) in acetone (2 ml) and the mixture stood overnight at room temperature. The resultant crystalline solid was filtered off and washed with acetone, then diethyl ether, to afford the title compound as the hydrochloride salt. (153 mg; 84%). MS: m/z=368.

The following compounds were prepared in a similar manner.

| | MS (MH+) |
|---|---|
| 4-Bromo-N-[4-methoxy-3-(4-methylpiperazin-1-yl)phenyl]benzenesulfonamide (E2) | 441 |
| N-[4-Methoxy-3-(4-methylpiperazin-1-yl)phenyl]-2-thiophenesulfonamide (E3) | 368 |
| N-[4-Methoxy-3-(4-methylpiperazin-1-yl)phenyl]-5-(pyridin-2-yl)-2-thiophenesulfonamide (E4) | 445 |
| 2,5-Dichloro-N-[4-methoxy-3-(4-methylpiperazin-1-yl)phenyl]-3-thiophenesulfonamide (E5) | 436/438 |
| 4-Bromo-5-chloro-N-[4-methoxy-3-(4-methylpiperazin-1-yl)phenyl]-2-thiophenesulfonamide (E6) | 482 |
| N-[4-Methoxy-3-(4-methylpiperazin-1-yl)phenyl]benzenesulfonamide (E7) | 362 |
| 3-Bromo-5-chloro-N-[4-methoxy-3-(4-methylpiperazin-1-yl)phenyl]-2-thiophenesulfonamide (E8) | 480/482 |
| N-[4-Methoxy-3-(4-methylpiperazin-1-yl)phenyl]benzylsulfonamide (E9) | 376 |
| 2-Bromo-N-[4-methoxy-3-(4-methylpiperazin-1-yl)phenyl]-benzenesulfonamide (E10) | 440/442 |
| 3-Bromo-N-[4-methoxy-3-(4-methylpiperazin-1-yl)phenyl]benzenesulfonamide (E11) | 440/442 |
| 3-Chloro-N-[4-methoxy-3-(4-methylpiperazin-1-yl)phenyl]-4-methyl-benzenesulfonamide (E12) | 410 |
| N-[4-Methoxy-3-(4-methylpiperazin-1-yl)phenyl]-trans-styrenesulfonamide (E13) | 388 |
| 3,4-Dichloro-N-[4-methoxy-3-(4-methylpiperazin-1-yl)phenyl]-benzenesulfonamide (E14) | 430 |
| 3,5-Dichloro-N-[4-methoxy-3-(4-methylpiperazin-1-yl)phenyl]benzenesulfonamide (E15) | 430/432 |
| N-[4-Methoxy-3-(4-methylpiperazin-1-yl)phenyl]-[2,1,3]benzothiadiazole-4-sulfonamide (E16) | 420 |
| 5-Chloro-N-[4-methoxy-3-(4-methylpiperazin-1-yl)phenyl]-3-methyl-2-benzothiophenesulfonamide (E17) | 466 |
| N-[4-Methoxy-3-(4-methylpiperazin-1-yl)phenyl]-2-methyl-5-nitro-benzenesulfonamide (E18) | 421 |
| N-[4-Methoxy-3-(4-methylpiperazin-1-yl)phenyl]-2-trifluoromethyl-benzenesulfonamide (E19) | 430 |
| N-[4-Methoxy-3-(4-methylpiperazin-1-yl)phenyl]-3-trifluoromethyl-benzenesulfonamide (E20) | 430 |
| 2,5-Dimethoxy-N-[4-methoxy-3-(4-methylpiperazin-1-yl)phenyl]-benzenesulfonamide (E21) | 422 |
| 4-Fluoro-N-[4-methoxy-3-(4-methylpiperazin-1-yl)phenyl]benzenesulfonamide (E22 | 380 |

-continued

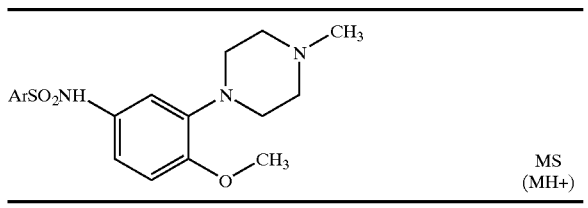

| | MS (MH+) |
|---|---|
| 4-Chloro-N-[4-methoxy-3-(4-methylpiperazin-1-yl)phenyl]benzenesulfonamide (E23) | 396 |
| 4-Iodo-N-[4-methoxy-3-(4-methylpiperazin-1-yl)phenyl]benzenesulfonamide (E24) | 488 |
| 4-Ethyl-N-[4-methoxy-3-(4-methylpiperazin-1-yl)phenyl]benzenesulfonamide (E25) | 390 |
| 4-tert-Butyl-N-[4-methoxy-3-(4-methylpiperazin-1-yl)phenyl]-benzenesulfonamide (E26) | 418 |
| 4-Isopropyl-N-[4-methoxy-3-(4-methylpiperazin-1-yl)phenyl]benzenesulfonamide (E27) | 404 |
| 4-tert-Amyl-N-[4-methoxy-3-(4-methylpiperazin-1-yl)phenyl]benzenesulfonamide (E28) | 432 |
| N-[4-Methoxy-3-(4-methylpiperazin-1-yl)phenyl]-4-trifluoromethoxy-benzenesulfonamide (E29) | 446 |
| 4-n-Butoxy-N-[4-methoxy-3-(4-methylpiperazin-1-yl)phenyl]benzenesulfonamide (E30) | 434 |
| N-[4-Methoxy-3-(4-methylpiperazin-1-yl)phenyl]-4-methylbenzenesulfonamide (E31) | 376 |
| 5-Chloro-N-[4-methoxy-3-(4-methylpiperazin-1-yl)phenyl]-2-thiophenesulfonamide (E32) | 402 |
| N-[4-Methoxy-3-(4-methylpiperazin-1-yl)phenyl]-1-naphthalenesulfonamide (E33) | 412 |
| N-[4-Methoxy-3-(4-methylpiperazin-1-yl)phenyl]-2-naphthalenesulfonamide (E34) | 412 |
| 5-(Dimethylamino)-N-[4-methoxy-3-(4-methylpiperazin-1-yl)phenyl]-1-naphthalenesulfonamide (E35) | 455 |
| 4-Bromo-N-[7-(4-methylpiperazin-1-yl)-2,3-dihydrobenzofuran-5-yl]-benzenesulfonamide (E36) | 452/454 |
| 4-Methoxy-N-[4-methoxy-3-(4-methylpiperazin-1-yl)phenyl]benzenesulfonamide (E37) | 392 |
| 4-n-Butyl-N-[4-methoxy-3-(4-methylpiperazin-1-yl)phenyl]benzenesulfonamide (E38) | 418 |
| 4-Amino-N-[4-methoxy-3-(4-methylpiperazin-1-yl)phenyl]-benzenesulfonamide (E39) | 377 |
| 2-Chloro-N-[4-methoxy-3-(4-methylpiperazin-1-yl)phenyl]benzenesulfonamide (E40) | 396 |
| 3-Chloro-N-[4-methoxy-3-(4-methylpiperazin-1-yl)phenyl]-benzenesulfonamide (E41) | 396 |
| 2,3,4-Trichloro-N-[4-methoxy-3-(4-methylpiperazin-1-yl)phenyl]-benzenesulfonamide (E42) | 464/466 |
| 4-Chloro-N-[4-methoxy-3-(4-methylpiperazin-1-yl)phenyl]-2,5-dimethyl-benzenesulfonamide (E43) | 424 |
| N-[4-Methoxy-3-(4-methylpiperazin-1-yl)phenyl]-3-methylbenzenesulfonamide (E44) | 376 |
| 2,5-Dibromo-3,6-difluoro-N-[4-methoxy-3-(4-methylpiperazin-1-yl)phenyl]-benzenesulfonamide (E45) | 556 |
| N-[4-Methoxy-3-(4-methylpiperazin-1-yl)phenyl]-2,3,5,6-tetramethyl-benzenesulfonamide (E46) | 418 |
| 5-Chloro-2-methoxy-N-[4-methoxy-3-(4-methylpiperazin-1-yl)phenyl]-benzenesulfonamide (E47) | 426 |
| 3-Fluoro-N-[4-methoxy-3-(4-methylpiperazin-1-yl)phenyl]benzenesulfonamide (E48) | 380 |
| 3,4-Difluoro-N-[4-methoxy-3-(4-methylpiperazin-1-yl)phenyl]benzenesulfonamide (E49) | 398 |
| 4-Chloro-N-[4-methoxy-3-(4-methylpiperazin-1-yl)phenyl]-3-nitro-benzenesulfonamide (E50) | 441 |
| 3-Chloro-N-[4-methoxy-3-(4-methylpiperazin-1-yl)phenyl]-2-methyl-benzenesulfonamide (E51) | 410 |
| N-[4-Methoxy-3-(4-methylpiperazin-1-yl)phenyl]-8-quinolinesulfonamide (E52) | 413 |
| N-[4-Methoxy-3-(4-methylpiperazin-1-yl)phenyl]-4-phenylbenzenesulfonamide (E53) | 438 |
| 3,4-Dimethoxy-N-[4-methoxy-3-(4-methylpiperazin-1-yl)phenyl]-benzenesulfonamide (E54) | 374 |
| N-[4-Methoxy-3-(4-methylpiperazin-1-yl)phenyl]-3,5-dimethyl-4-isoxazolesulfonamide (E55) | 381 |
| 4-Bromo-N-[4-methoxy-3-(4-ethylpiperazin-1-yl)phenyl]benzenesulfonamide (E56) | 454/456 |
| 2,3-Dichloro-N-[4-methoxy-3-(4-methylpiperazin-1-yl)phenyl]-benzenesulfonamide (E57) | 430 |

-continued

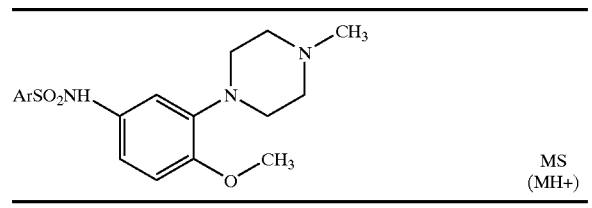

| | MS (MH+) |
|---|---|
| 5-Iodo-N-[4-methoxy-3-(4-methylpiperazin-1-yl)phenyl]-2-methyl-benzenesulfonamide (E58) | 502 |
| 3-Iodo-N-[4-methoxy-3-(4-methylpiperazin-1-yl)phenyl]benzenesulfonamide (E59) | 488 |
| 3-Iodo-N-[4-methoxy-3-(4-methylpiperazin-1-yl)phenyl]-4-methyl-benzenesulfonamide (E60) | 502 |
| 5-Chloronaphthalene-2-sulfonic acid [4-methoxy-3-(4-methylpiperazin-1-yl)phenyl] amide (E61) | 446 |
| 5-Chloronaphthalene-1-sulfonic acid [4-methoxy-3-(4-methylpiperazin-1-yl)phenyl] amide (E62) | 446 |
| 4-Chloronaphthalene-1-sulfonic acid [4-methoxy-3-(4-methylpiperazin-1-yl)phenyl] amide (E63) | 446 |
| 7-Chloronaphthalene-1-sulfonic acid [4-methoxy-3-(4-methylpiperazin-1-yl)phenyl] amide (E64) | 446 |
| 5-Chloro-2-methylbenzo[b]thiophene-3-sulfonic acid [4-methoxy-3-(4-methylpiperazin-1-yl)phenyl] amide (E65) | 466 |
| Benzofuran-2-sulfonic acid [4-methoxy-3-(4-methylpiperazin-1-yl)phenyl] amide (E66) | 402 |
| 1-Methyl-1H-indole-2-sulfonic acid [4-methoxy-3-(4-methylpiperazin-1-yl)phenyl] amide (E67) | 415 |
| 2,3-Dichloro-N-[4-methoxy-3-(4-methylpiperazin-1-yl)phenyl]-benzenesulfonamide (E138) | 430/432 |

Preparation of Aryl-N-(4-methoxy-3-piperazin-1-ylphenyl)benzene Sulfonamides

These compounds were prepared using one of the three general methods as outlined below.

GENERAL METHOD 1

Examples 68–75 were prepared by the following general method from the corresponding N-methyl piperazine analogues:

A solution of 1-chloroethylchloroformate (1.7 mmol) and the appropriate N-[4-methoxy-3-(4-methyl-1-piperazinyl) phenyl]-arylsulfonamide (0.34 mmol) in 1,2-dichloroethane (4 ml) was refluxed for 0.75 h, cooled, diluted with diisopropylethylamine (1.7 mmol) and refluxed for a further 2.5 hrs. The solution was concentrated to a residue which was re-dissolved in methanol, refluxed for 1 hr and then stirred at room temperature for 24 h. The mixture was concentrated, and the residue partitioned between ethyl acetate and aqueous sodium bicarbonate solution.

The organic layer was dried, concentrated to a residue and purified by column chromatography on silica gel using a methanol/dichloromethane solvent gradient. The hydrochloride salt of the product was prepared by dissolving the pure material from chromatography in acetone/dichloromethane and acidifying with ethereal HCl.

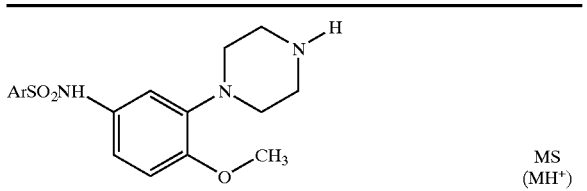

| | MS (MH+) |
|---|---|
| 5-Pyridin-2-ylthiophene-2-sulfonic acid (4-methoxy-3-piperazin-1-ylphenyl) amide (E68) | 431 |
| N-(4-Methoxy-3-piperazin-1-ylphenyl)-3-trifluoromethylbenzenesulfonamide (E69) | 416 |
| 3-Iodo-N-(4-methoxy-3-piperazin-1-ylphenyl)benzenesulfonamide (E70) | 474 |
| 3,5-Dimethylisoxazole-4-sulfonic acid (4-methoxy-3-piperazin-1-ylphenyl) amide (E71) | 367 |
| 3,5-Dichloro-N-(4-methoxy-3-piperazin-1-ylphenyl)benzenesulfonamide (E72) | 416/418 |
| 2,5-Dibromo-3,6-difluoro-N-(4-methoxy-3-piperazin-1-ylphenyl)benzenesulfonamide (E73) | 542 |
| Naphthalene-1-sulfonic acid (4-methoxy-3-piperazin-1-ylphenyl) amide (E74) | 398 |
| 2-Bromo-5-chlorothiophene-2-sulfonic acid (4-methoxy-3-piperazin-1-ylphenyl) amide (E75) | 466/468 |

GENERAL METHOD 2

Examples 76–86 were prepared by the following general method from the appropriate N-Boc derivative (D4–D14):

A stirred solution of the appropriate N-Boc derivative (D4–D14) (10.3 mmol) in methanol (100 ml) and 1M ethereal HCl (51.6 ml) was heated at 60° C. for 1.5 h. The mixture was then concentrated and the residue stirred with acetone to afford the following title compounds as the hydrochloride salts.

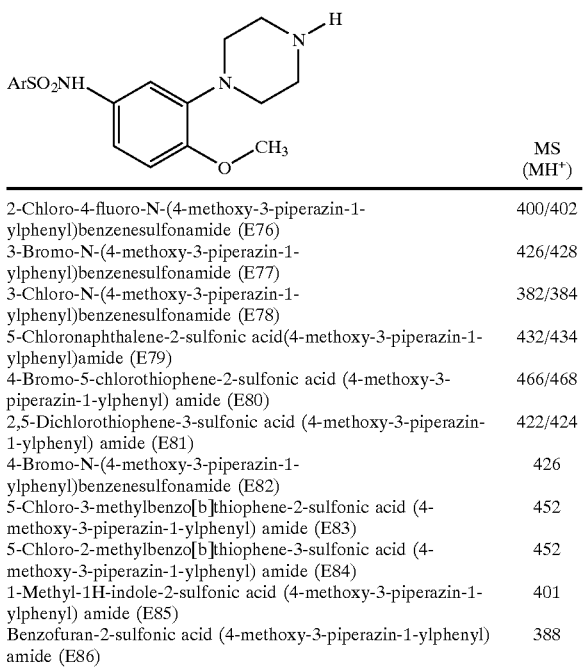

| | MS (MH+) |
|---|---|
| 2-Chloro-4-fluoro-N-(4-methoxy-3-piperazin-1-ylphenyl)benzenesulfonamide (E76) | 400/402 |
| 3-Bromo-N-(4-methoxy-3-piperazin-1-ylphenyl)benzenesulfonamide (E77) | 426/428 |
| 3-Chloro-N-(4-methoxy-3-piperazin-1-ylphenyl)benzenesulfonamide (E78) | 382/384 |
| 5-Chloronaphthalene-2-sulfonic acid(4-methoxy-3-piperazin-1-ylphenyl)amide (E79) | 432/434 |
| 4-Bromo-5-chlorothiophene-2-sulfonic acid (4-methoxy-3-piperazin-1-ylphenyl) amide (E80) | 466/468 |
| 2,5-Dichlorothiophene-3-sulfonic acid (4-methoxy-3-piperazin-1-ylphenyl) amide (E81) | 422/424 |
| 4-Bromo-N-(4-methoxy-3-piperazin-1-ylphenyl)benzenesulfonamide (E82) | 426 |
| 5-Chloro-3-methylbenzo[b]thiophene-2-sulfonic acid (4-methoxy-3-piperazin-1-ylphenyl) amide (E83) | 452 |
| 5-Chloro-2-methylbenzo[b]thiophene-3-sulfonic acid (4-methoxy-3-piperazin-1-ylphenyl) amide (E84) | 452 |
| 1-Methyl-1H-indole-2-sulfonic acid (4-methoxy-3-piperazin-1-ylphenyl) amide (E85) | 401 |
| Benzofuran-2-sulfonic acid (4-methoxy-3-piperazin-1-ylphenyl) amide (E86) | 388 |

EXAMPLE 83
5-Chloro-3-methylbenzo[b]thiophene-2-sulfonic Acid (4-Methoxy-3-piperazin-1-ylphenyl)amide Hydrochloride (E83)

A stirred suspension of 5-chloro-3-methylbenzo[b]thiophene-2-sulfonic acid (4-methoxy-3-(4-tert-butoxycarbonylpiperazin-1-yl)phenylamide (D10) (193 g) in tetrahydrofuran (820 ml) and concentrated hydrochloric acid (180 ml) was heated at reflux for 1.75 h after which time a solution was obtained. The solution was concentrated and the residue dissolved in hot ethanol (600 ml). Upon cooling, a solid precipitated which was filtered and recrystallised (ethanol/water 1:1) to give the title compound (E83) as a white solid, m.p. 276–280° C. (dec.) (142 g, 83%). $\delta_H$ (250 MHz, D6-dmso) 2.29 (3H, s), 2.90 (4H, br s), 3.01 (4H, br s), 3.55 (3H, s), 6.54–6.71 (3H. m), 7.42 (1H, d, J 8.8 Hz), 7.85 (1H, s), 7.93 (1H, d, J 8.8 Hz), 9.03 (2H, br s), 10.3 (1H, br s). MH+ 452.

GENERAL METHOD 3

Examples 87–94 were prepared by the following general method:

A solution of the appropriate arylsulfonyl chloride (0.47 mmol) and the aniline from D16 (0.47 mmol) in dichloromethane (4 ml) and pyridine (2.4 mmol) was stirred for 18 h at room temperature. The mixture was washed with 1M aqueous HCl then water. The layers were separated and to the organic one was added 4.4M aqueous KOH (1.4 mmol) with vigorous stirring for 18 h. To the heterogeneous mixture was then added an equal volume of 10% phosphate buffer. The layers were again separated and the organic phase was dried and diluted with 1M ethereal HCl to afford the hydrochloride salts of the following compounds as a precipitate.

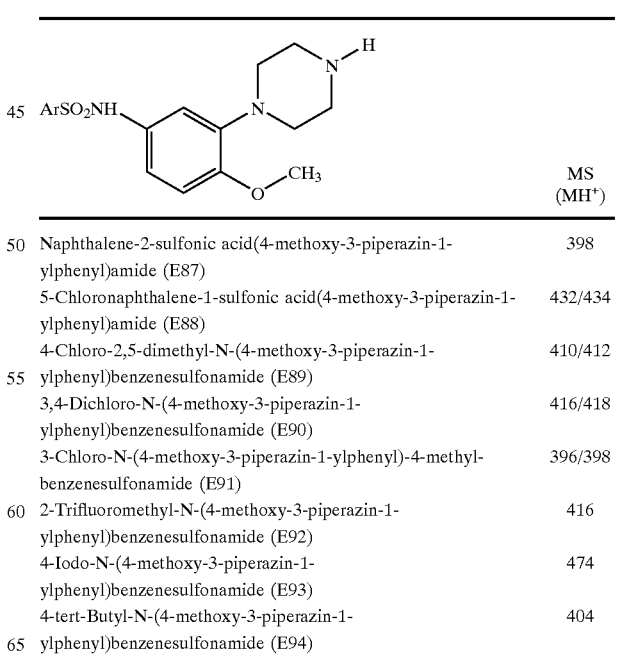

| | MS (MH+) |
|---|---|
| Naphthalene-2-sulfonic acid(4-methoxy-3-piperazin-1-ylphenyl)amide (E87) | 398 |
| 5-Chloronaphthalene-1-sulfonic acid(4-methoxy-3-piperazin-1-ylphenyl)amide (E88) | 432/434 |
| 4-Chloro-2,5-dimethyl-N-(4-methoxy-3-piperazin-1-ylphenyl)benzenesulfonamide (E89) | 410/412 |
| 3,4-Dichloro-N-(4-methoxy-3-piperazin-1-ylphenyl)benzenesulfonamide (E90) | 416/418 |
| 3-Chloro-N-(4-methoxy-3-piperazin-1-ylphenyl)-4-methyl-benzenesulfonamide (E91) | 396/398 |
| 2-Trifluoromethyl-N-(4-methoxy-3-piperazin-1-ylphenyl)benzenesulfonamide (E92) | 416 |
| 4-Iodo-N-(4-methoxy-3-piperazin-1-ylphenyl)benzenesulfonamide (E93) | 474 |
| 4-tert-Butyl-N-(4-methoxy-3-piperazin-1-ylphenyl)benzenesulfonamide (E94) | 404 |

EXAMPLES 95–108

The dihydrobenzofuran derivative, below,

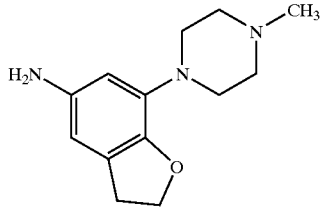

was prepared as described previously WO 95/11243 (Glaxo) and coupled with the appropriate aryl sulfonyl chlorides in the manner described in Example 1 to afford the following compounds:

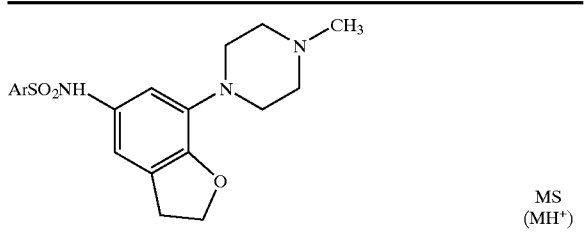

| | MS (MH+) |
|---|---|
| Naphthalene-1-sulfonic acid [7-(4-methylpiperazin-1-yl)-2,3-dihydrobenzofuran-5-yl] amide (E95) | 424 |
| Thiophene-2-sulfonic acid [7-(4-methylpiperazin-1-yl)-2,3-dihydrobenzofuran-5-yl] amide (E96) | 380 |
| 5-Chlorothiophene-2-sulfonic acid [7-(4-methylpiperazin-1-yl)-2,3-dihydrobenzofuran-5-yl] amide (E97) | 414/416 |
| 5-Pyridin-2-ylthiophene-2-sulfonic acid [7-(4-methylpiperazin-1-yl)-2,3-dihydrobenzofuran-5-yl] amide (E98) | 457 |
| 2,5-Dichlorothiophene-3-sulfonic acid [7-(4-methylpiperazin-1-yl)-2,3-dihydrobenzofuran-5-yl] amide (E99) | 448/450 |
| 4-Bromo-5-chlorothiophene-2-sulfonic acid [7-(4-methylpiperazin-1-yl)-2,3-dihydrobenzofuran-5-yl] amide (E100) | 492/494 |
| 3-Bromo-5-chlorothiophene-2-sulfonic acid [7-(4-methylpiperazin-1-yl)-2,3-dihydrobenzofuran-5-yl] amide (E101) | 492/494 |
| 4-Chloro-2,5-dimethyl-N-[7-(4-methylpiperazin-1-yl)-2,3-dihydrobenzofuran-5-yl]benzenesulfonamide (E102) | 436 |
| 5-Chloro-3-methylbenzo[b]thiophene-2-sulfonic acid [7-(4-methylpiperazin-1-yl)-2,3-dihydrobenzofuran-5-yl] amide (E103) | 478 |
| Naphthalene-2-sulfonic acid [7-4-methylpiperazin-1-yl)-2,3-dihydrobenzofuran-5-yl] amide (E104) | 424 |
| 3-Bromo-N-[7-(4-methylpiperazin-1-yl)-2,3-dihydrobenzofuran 5-yl]benzenesulfonamide (E105) | 452/454 |
| 3,5-Dichloro-N-[7-(4-methylpiperazin-1-yl)-2,3-dihydrobenzofuran-5-yl]benzenesulfonamide (E106) | 442/444 |
| 4-tert-Butyl-N-[7-(4-methylpiperazin-1-yl)-2,3-dihydrobenzofuran-5-yl]benzenesulfonamide (E107) | 430 |
| 2,5-Dibromo-3,6-difluoro-N-[7-(4-methylpiperazin-1-yl)-2,3-dihydrobenzofuran-5-yl]benzenesulfonamide (E108) | 568 |

EXAMPLES 109–110

The following compounds were prepared from the corresponding N-methyl analogues by the general method described for Examples 68–75:

| | MS (MH+) |
|---|---|
| 2,5-Dibromo-3,6-difluoro-N-(7-piperazin-1-yl-2,3-dihydrobenzofuran-5-yl)benzenesulfonamide (E109) | 554 |
| 4-Chloro-2,5-dimethyl-N-(7-piperazin-1-yl-2,3-dihydrobenzofuran-5-yl)benzenesulfonamide (E110) | 422 |

EXAMPLE 111

5-Chloro-3-methylbenzo[b]thiophene-2-sulphonic Acid [3-(4-Cyclopropylmethyl-piperazin-1-yl)-4-methoxy-phenyl]amide (E111)

To a solution of 3-(4-benzyl-piperazin-1-yl)-4-methoxy-phenylamine (D22) (1 mmol) in acetone (5 ml) was added 5-chloro-3-methylbenzothiophene-2-sulphonyl chloride (1 mmol). Stirring was continued at room temperature for 14 hrs. The hydrochloride salt of the sulphonamide was collected by filtration, triturated with diethyl ether and dried in vacuo in 42% yield. Found MH+ 506/508.

EXAMPLE 112

5-Chloro-3-methylbenzo[b]thiophene-2-sulphonic Acid [3-(4-Benzyl-piperazin-1-yl)-4-methoxyphenyl]-amide (E112)

The title compound was prepared in 32% yield using the procedure outlined for E111. Found MH+ 542/544

EXAMPLE 113

5-Chloro-3-methyl-benzo[b]thiophene-2-sulphonic Acid [4-Hydroxy-3-(4-methyl-piperazin-1-yl)-phenyl]-amide (E113)

To a suspension of boron tribromide dimethyl sulphide complex (620 mg, 2 mmol) in 1,2 dichloroethane (30 ml) under argon was added 5-chloro-3-methyl-benzo[b] thiophene-2-sulphonic acid [4-methoxy-3-(4-methyl-piperazin-1-yl)phenyl]amide (E17) (0.2 mmol). The reaction mixture was heated to reflux for 12 hrs, cooled, quenched by the addition of water (20 ml) and partitioned between saturated aqueous sodium bicarbonate and dichloromethane. The organic phase was dried over sodium sulphate and concentrated in vacuo. The residue was purified by chromatography on silica gel to afford the title compound (E113). Found MH+ 452/454

General Method for the Preparation of Examples 114–116

A solution of 5-chloro-3-methyl-benzo[b]thiophene-2-sulphonic acid [4-hydroxy-3-(4-methyl-piperazin-1-yl)- phenyl]-amide (E113) (100 mg, 0.22 mmol) and 18-Crown-6 (58 mg, 0.22 mmol) in DMF (0.5 ml) was added to potassium hydride (35% dispersion in mineral oil, 50 mg, 0.44 mol) at room temperature under argon. After 10 minutes a solution of the alkylating agent (0.22 mmol) in DMF (0.3 ml) was added and stirring was continued for 12 hrs. The reaction mixture was quenched with water and then concentrated in vacuo before partitioning between saturated aqueous sodium bicarbonate and dichloromethane. The organic phase was dried over sodium sulphate and concentrated in vacuo. The residue was purified by chromatography on silica to afford the following alkylated final compounds.

EXAMPLE 114

5-Chloro-3-methyl-benzo[b]thiophene-2-sulphonic Acid [4-Benzyloxy-3-(4-methyl-piperazin-1-yl)-phenyl]-amide (E114)

Prepared in 22% yield using benzyl bromide. Found $MH^+$ 542/544.

EXAMPLE 115

5-Chloro-3-methyl-benzo[b]thiophene-2-sulphonic Acid [4-Ethoxy-3-(4-methyl-piperazin-1-yl)-phenyl]-amide (E115)

Prepared in 28% yield using the procedure outlined above using ethyl iodide. Found $MH^+$ 480/482.

EXAMPLE 116

5-Chloro-3-methyl-benzo[b]thiophene-2-sulphonic Acid [4-Isopropoxy-3-(4-methyl-piperazin-1-yl)-phenyl]-amide (E116)

Prepared in 20% yield using the procedure outlined above using 2-iodopropane. Found $MH^+$ 494/496.

EXAMPLE 117

5-Chloro-3-methyl-benzo[b]thiophene-2-sulphonic Acid [4-Methoxy-3-(1-methyl-pyrrolidin-3-yloxy)-phenyl]-amide (E117)

The title compound was prepared in 48% yield from D25 and 5-chloro-3-methylbenzothiophene-2-sulphonyl chloride as described for E111. Found $MH^+$ 467/469.

EXAMPLE 118

Naphthalene-2-sulfonic Acid [2-Bromo-5-(4-methylpiperazin-1-yl)phenyl]amide (E118)

The title compound (E118) was prepared from naphthalene-2-sulfonyl chloride (100 mg, 0.44 mmol) and 2-bromo-5-(4-methylpiperazin-1-yl)phenylamine (D27) (120 mg, 0.44 mmol) using the method of Example 1 (85 mg, 35%) $MH^+$=460/462.

EXAMPLE 119

5-Chloro-3-methylbenzo[b]thiophene-2-sulfonic Acid [4-Chloro-3-(4-methylpiperazin-1-yl)phenyl] amide (E119).

The title compound (E119) was prepared from 4-chloro-3-(4-methylpiperazin-1-yl)benzenamine (EP 0533267A, intermediate 42) (50 mg, 0.22 mmol) and 5-chloro-3-methylbenzo[b]thiophene-2-sulfonyl chloride (62 mg, 0.22 mmol) using the method of Example 1 (49 mg, 44%) $MH^+$=470/472.

EXAMPLE 120

Naphthalene-2-sulfonic Acid [4-Bromo-3-(4-methylpiperazin-1-yl)phenyl]amide (E120)

The title compound (E120) was prepared from 4-bromo-3-(4-methylpiperazin-1-yl)benzenamine (EP 0533267A, intermediate 61) (600 mg, 2.23 mmol) and naphthalene-2-sulfonyl chloride (504 mg, 2.23 mmol) using the method of Example 1 (939 mg, 92%) $MH^+$=460/462.

EXAMPLE 121

5-Chloro-3-methylbenzo[b]thiophene-2-sulfonic Acid[3-(2-Dimethylaminoethoxy)-4-iodophenyl] amide (E121).

The title compound was prepared from 3-(2-dimethylaminoethoxy)-4iodoaniline (WO95/15954, Description 50) (109 mg, 0.36 mmol) and 5-chloro-3-methylbenzo[b]thiophene-2-sulfonyl chloride (100 mg, 0.36 mmol) using the method of Example 1 (70 mg, 36%) $MH^+$=551/553.

EXAMPLE 122

5Chloro-3-methylbenzo[b]thiophene-2-sulfonic Acid [1-(2-Dimethylaminoethyl)-2,3-dihydro-1H-indol-6-yl]amide (E122)

The title compound (E122) was prepared from 1-(2-dimethylaminoethyl)-2,3-dihydro-1H-indol-6-ylamine (WO95/32967 Description 4) (100 mg, 0.49 mmol) and 5-chloro-3-methylbenzo[b]thiophene-2-sulfonyl chloride (137 mg, 0.49 mmol) using the method of Example 1 (40 g, 18%) $MH^+$=450/452.

EXAMPLE 123

1-(5-Chloro-3-methylbenzo[b]thiophene2-sulfonyl)-6-(4-methylpiperazin-1-yl)-2,3-dihydro-1H-indole (E123)

The title compound (E123) was prepared from 6-(4-methylpiperazin-1-yl)-2,3-dihydro-1H-indole (prepared from 3-nitroaniline, using methodology of WO95/06637 Intermediate 3) (39 mg, 0.18 mmol) and 5-chloro-3-methylbenzo[b]thiophene-2-sulfonyl chloride (50 mg; 0.18 mmol) using the method of Example 1 (75 mg, 84%) $MH^+$=462/464.

EXAMPLE 124

1-(5-Chloro-3-methylbenzo[b]thiophene-2-suffonyl)-5-methoxy-6-(4-methylpiperazin-1-yl)-2,3-dihydro-1H-indole (E124)

The title compound (E124) was prepared from 5-methoxy-6-(4-methylpiperazin-1-yl)-2,3-dihydro-1H-indole (WO95106637 intermediate 3) (99 mg, 0.4 mmol) and 5-chloro-3-methylbenzo[b]thiophene-2-sulfonyl chloride (113 mg, 0.4 mmol) using the method of Example 1 (194 mg, 92%) $MH^+$=492/494.

EXAMPLE 125

5-Chloro-3-methylbenzo[b]thiophene-2-sulfonic Acid[4-Methoxy-2-methyl-3-(4-methylpiperazin-1-yl)phenyl]amide (E125)

The title compound (E125) was prepared from 4-methoxy-2-methyl-3-(4-methylpiperazin-1-yl)

phenylamine (D33) (58 mg, 0.247 mmol) and 5-chloro-3-methylbenzo[b]thiophene-2-sulfonyl chloride (70 mg, 0.247 mmol) using the method of Example 1 (103 mg, 81%). MH$^+$=480/482.

EXAMPLE 126

5-Chloro-3-methylbenzo[b]thiophene-2-sulfonic Acid[2-(2-Hydroxyethyl)-4-methoxy-3-(4-methylpiperazin-1-yl)phenyl]amide (E126)

The title compound (E126) was prepared from 2-[6-amino-3-methoxy-2-(4-methylpiperazin-1-yl)phenyl]ethanol (D32) (74 mg, 0.28 mmol) and 5-chloro-3-methylbenzo[b]thiophene-2-sulfonyl chloride (78 mg, 0.28 mmol) using the method of Example 1 (18 mg, 13%). MH$^+$=510.

EXAMPLE 127

1-(5-Chloro-3-methylbenzo[b]thiophene-2-sulfonyl)-5-methoxy-4-(4-methylpiperazin-1-yl)-2,3-dihydro-1H-indole Hydrochloride (E127)

A mixture of 5-chloro-3-methylbenzo[b]thiophene-2-sulfonic acid[2-(2-hydroxyethyl)-4-methoxy-3-(4-methylpiperazin-1-yl)phenyl]amide (E126) (218 mg, 0.25 mmol) and triphenyl phosphine (183 mg, 0.375 mmol) in dry THF (5 ml) under argon, was treated with a solution of diethyl azodicarboxylate (110 mg, 0.375 mmol) in dry THF (5 ml). The mixture was stirred overnight at room temperature. The solvent was evaporated under reduced pressure, and the residue partitioned between dilute hydrochloric acid and ethyl acetate. The acidic layer was basified with 40% sodium hydroxide and re-extracted with ethyl acetate. The organic phase was dried (Na$_2$SO$_4$) and evaporated under reduced pressure to give the crude product, which was purified by chromatography on silica gel, eluting with methanol and dichloromethane and the hydrochloride salt was formed (52 mg, 23%) MH$^+$=492/494.

EXAMPLE 128

5-Chloro-3-methylbenzo[b]thiophene-2-sulfonic Acid[3-Methoxy-4-(4-methylpiperazin-1-yl)phenyl]amide (E128)

A solution of 3-methoxy-4-(4-methylpiperazin-1-yl)phenylamine (D35) (50 mg, 0.23 mmol) and 5-chloro-3-methylbenzo[b]thiophene-2-sulfonyl chloride (64 mg, 0.23 mmol) in dichloromethane (2 ml) was allowed to stand at room temperature overnight. The reaction mixture was diluted with dichloromethane and washed with potassium carbonate (aq), which was back-extracted with further dichloromethane. The combined organic phases were dried (Na$_2$SO$_4$) and evaporated under reduced pressure to give a crude product, which was purified by chromatography on silica gel, eluting with methanol and dichloromethane. This gave the title compound (E128) as an off-white solid (36 mg, 34%) MH$^+$=466.

EXAMPLE 129

4-Bromo-N-[4-methoxy-3-(1-methyl-1,2,3,6-tetrahydropyridin-4-yl)phenyl]benzenesulfonamide (E129)

The title compound (E129) was prepared from 4-methoxy-3-(1-methyl-1,2,3,6-tetrahydropyridin-4-yl)phenylamine (free base of D39) (107 mg; 0.49 mmol) and 4-bromobenzenesulfonylchloride (125 mg, 0.49 mmol) using the method of Example 1 (179 mg, 77%) MH$^+$=437/439.

EXAMPLE 130

5-Chloro-3-methylbenzo[b]thiophene-2-sulfonic Acid [4-Methoxy-3-(1-methyl-1,2,3,6-tetrahydropyridin-4-yl)phenyl]amide (E130)

The title compound (E130) was prepared from 4-methoxy-3-(1-methyl-1,2,3,6-tetrahydropyridin-4-yl)phenylamine (free base of D39) (100 mg, 0.46 mmol) and 5-chloro-3-methylbenzo[b]thiophene-2-sulfonyl chloride (129 mg, 0.46 mmol) using the method of Example 1 (177 mg, 77%). MH$^+$=463/465.

EXAMPLE 131

5-Chloro-3-methylbenzo[b]thiophene-2-sulfonic Acid [4-Methoxy-3-(1-methylpiperidin-4-yl)phenyl]amide (E131)

The title compound (E131) was prepared from 4-methoxy-3-(1-methylpiperidin-1-yl)phenylamine (D38) (150 mg, 0.68 mmol) and 5-chloro-3-methylbenzo[b]thiophene-2-sulfonyl chloride (192 mg, 0.68 mmol) using the method of Example 1 (108 mg, 32%) MH$^+$=465/467.

EXAMPLE 132

Naphthalene-2-sulfonic Acid [3-(4-Methylpiperazin-1-yl)phenyl]amide (E132)

The title compound (E132) was prepared from 3-(4-methylpiperazin-1-yl)benzenamine and naphthalene-2-sulfonyl chloride according to the method of Example 1 MH$^+$=382.

Preparation of Aryl-N-(4-methoxy-3-piperazin-1-yl)-benzenesulfonamide Hydrochlorides on Solid Phase (Examples 133–137)

The resin from Description 42 was stirred for 24 h at room temperature with a solution of 1-chloroethylchloroformate (1.1 mmol) in dichloromethane (2 ml) then filtered and washed with dichloromethane. The filtrate was concentrated and the residue redissolved in methanol (3 ml) and the solution refluxed for 5 h. The solution was then concentrated to yield the title compound.

The following compounds were prepared as described above:

| compound | MH$^+$ |
| --- | --- |
| 2,3,4-Trichloro-N-(4-methoxy-3-piperazin-1-yl-phenyl)benzenesulfonamide (E133) | 450/452 |
| 2,3-Dichloro-N-(4-methoxy-3-piperazin-1-yl-phenyl)benzenesulfonamide (E134) | 416/418 |
| 3-Chloro-2-methyl-N-(4-methoxy-3-piperazin-1-yl-phenyl)benzenesulfonamide (E135) | 396/398 |
| 4-Chloro-N-(4-methoxy-3-piperazin-1-yl-phenyl)benzenesulfonamide (E136) | 382/384 |
| 5-Bromo-thiophene-2-sulfonic acid (4-methoxy-3-piperazin-1-yl-phenyl)-amide (E137) | 432/434 |

EXAMPLE 138

2,3-Dichloro-N-[4-methoxy-3-(4-methylpiperazin-1-yl)phenyl]-benzenesulfonamide (E138) MS(MH+) 430/432 was prepared according to the general method of Example 1

EXAMPLES 139–141

The following compounds were prepared in an analagous way to Examples 68–75

| | MS(MH+) |
|---|---|
| 1-(5-Chloro-3-methylbenzo[b]thiophene-2-sulfonyl)-5-phenyl-6-piperazin-1-yl-2,3-dihydro-1H-indole (E139) | 524/526 |
| 5-Chloro-1-(5-chloro-3-methylbenzo[b]thiophene-2-sulfonyl)-6-piperazin-1-yl-2,3-dihydro-1H-indole (E140) | 482/484 |
| 1-(5-Chloro-3-methylbenzo[b]thiophene-2-sulfonyl)-7-piperazin-yl-1,2,3,4-tetrahydroquinoline (E141) | 462/464 |

EXAMPLE 142

5-Chloro-3-methylbenzo[b]thiophene-2-sulfonic Acid[4-Methyl-3-(4-methylpiperazin-1-yl)phenyl]amide (E142)

The title compound (E142) was prepared from 5-chloro-3-methylbenzo[b]thiophene-2-sulfonyl chloride and 4-methyl-3-(4-methylpiperazin-1-yl)benzenamine according to the method of Example 1 MH$^+$32 448/450.

EXAMPLE 143

(S)-5-Chloro-3-methylbenzo[b]thiophene-2-sulfonic Acid[4-Methoxy-3-(1-methylpyrrolidin-2-ylmethoxy)phenyl]amide (E143)

A solution of (S)-1-methyl-2-(2-methoxy-5-aminophenoxy)pyrrolidine (D44) (0.22 g; 9.3×10$^{-4}$ mol) in DCM (10 ml) containing DIPEA (0.162 ml; 9.3×10$^{-4}$ mol) was treated with 5-chloro-3-methylbenzene-2-sulphonyl chloride (0.262; 9.3×10$^{-4}$ mol) portionwise. Stirred at RT for 18 h, then evaporated in vacuo and the residue purified by Sep-Pak Silica-gel column chromatography with 2% MeOH/DCM as eluent to yield the title compound as a clear, colourless gum (0.14 g; 31%). This was converted to the hydrochloride salt with HCl in Et2O (0.31 ml of a 1.0M solution) with trituration yielding the title compound (E143) as the salt as a white, crystalline solid (0.13 g) MH$^+$=481/483.

Method for assay of 5-HT6 antagonistic activity:

The test compounds were dissolved in polyethylene glycol:dimethyl sulphoxide (1:1) at 1 or 10 mM and diluted to 0.1 mM using 5 mM tris buffer (pH 7.7 @25° C.). Dissolution was assisted by addition of 0.02 ml 5M HCl plus heating to 40° C. and sonication for 10 minutes. Serial dilutions of drugs in the same buffer were carried out using either a TECAN 5052 or Biomek 2000 Workstation. Samples of the diluted test compounds (0.05 ml) were mixed with 0.05 ml of radio-ligand [$^3$H]-LSD prepared in the incubation buffer, and 0.4 ml of a suspension of a preparation of the washed membranes of HeLa_5HT6 cells (acquired from Dr. D. Sibley, NIH, Bethesda, see Ref 1)(see Table 1), also in the incubation buffer. The details of the incubation conditions for each assay are shown in Table 2. The incubation buffer was 50 mM Trizma (Sigma, UK) pH7.7 @25° C., 4 mM MgCl$_2$.

After incubation at 37° C., the mixtures were filtered using a Packard Filtermate in Packard TopCount format. Filters were washed with 4×1 ml aliquots of ice-cold incubation buffer. Filters were dried and impregnated with 0.04 ml of Microscint 20 (Packard). IC$_{50}$ values were estimated from the counts per minute using a four parameter logistic curve fit within EXCEL (2). K$_i$ values were calculated using the method of Cheng and Prusoff(3). pIC$_{50}$ and pK$_i$ are the negative log10 of the molar IC$_{50}$ and K$_i$ respectively.

TABLE 1

Details of the methods used to prepare membranes for binding assays

| 1st resuspension cells/ml | spin/ resuspension 1, 2, 3 | Incubation before final spin | protein conc. in stored aliquots | cells/ml in stored aliquots |
|---|---|---|---|---|
| 7 × 10$^7$ | Yes | 20 min at 37° C. | 4 mg/ml | 1.0 × 10$^8$ |

TABLE 2

Summary of receptor binding assay conditions

| protein (ug/ sample) | radio-ligand [$^3$H]-LSD (nM) | Specific Activity (Ci/mmol) | Non-Specific Definition | Kd (nM) |
|---|---|---|---|---|
| 40 | 2.0 | 83 | Methiothepin | 3.1 |

REFERENCES

1. MONSMA, F. J., SHEN, Y., WARD, R. P., HAMBLIN, M. W., SIBLEY, D. R., 1993. Cloning and expression of a novel serotonin receptor with high affinity for tricyclic psychotropic drugs. *Mol. Pharmacol.*, 43, 320–327.
2. BOWEN, W. P., JERMAN, J. C., 1995. Nonlinear regression using spreadsheets. *Trends in Pharmacol. Sci.*, 16,413–417.
3. CHENG, Y. C., PRUSSOF, W. H., 1973. Relationship between inhibition constant (Ki) and the concentration of inhibitor which causes 50% inhibition (IC50) of an enzymatic reaction. *Biochem. Pharmacol.*, 92, 881–894.

The compounds of Examples 11, 15, 17, 61, 65, 70, 72, 77, 78, 79, 83, 84, 87 and 90 all showed particularly good selective 5-HT6 receptor antagonist activity, having pKi values above 8.0 at human cloned 5-HT6 receptors.

What is claimed is:

1. A compound of formula (I) or a salt thereof:

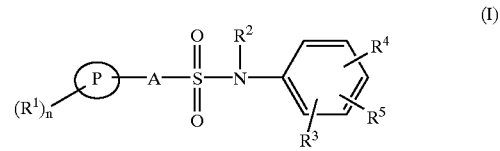

wherein:

P is benzothiophene, benzothiadiazole, quinoline, benzofuran or indole;

A is a single bond, a C$_{1-6}$alkylene or a C$_{1-6}$alkenylene group;

R$^1$ is halogen, C$_{1-6}$alkyl optionally substituted by one or more halogen atoms, C$_{3-6}$cycloalkyl, COC$_{1-6}$alkyl, C$_{1-6}$alkoxy, OCF$_3$, hydroxy, hydroxyC$_{1-6}$alkyl, hydroxyC$_{1-6}$alkoxy, C$_{1-6}$alkoxyC$_{1-6}$alkoxy, nitro, amino, C$_{1-6}$alkylamino or C$_{1-6}$dialkylamino, cyano or R$^1$ is phenyl or naphthyl;

n is 0, 1, 2, 3, 4, 5, or 6;

R$^2$ is hydrogen, C$_{1-6}$alkyl or aryl C$_{1-6}$alkyl or R$^2$ is linked to R$^3$ to form a group (CH$_2$)$_2$ or (CH$_2$)$_3$;

R$^3$ is a group R$^5$ or together with R$^5$ forms a group (CH$_2$)$_2$O or (CH$_2$)$_3$O or R$^3$ is linked to R² to form a group (CH₂)₂ or (CH₂)₃;

R⁴ is an N-piperazine ring optionally substituted by C$_{1-6}$alkyl; and

R⁵ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, nitro, trifluoromethyl, cyano or aryl.

2. A compound according to claim 1 in which P is benzothiophene.

3. A compound according to claim 1 in which R¹ is halogen or C$_{1-6}$alkyl optionally substituted by one or more halogen atoms.

4. A compound according to claim 3 in which R² is hydrogen.

5. A compound according to claim 1 in which R⁴ is an unsubstituted piperazine ring.

6. A compound according to claim 5 in which R5 is C$_{1-6}$alkoxy.

7. A compound according to claim 6 in which R⁵ is para with respect to the sulphonamide linkage.

8. A compound according to claim 7 in which P-A is 5-chloro-3-methyl-benzo[2]thiophen-2-yl.

9. A compound according to claim 1 which is:

N-[4-Methoxy-3-(4-methylpiperazin-1-yl)phenyl]-[2,1,3] benzothiadiazole-4-sulfonamide, N-[4-Methoxy-3-(4-methylpiperazin-1-yl)phenyl]-8-quinolinesulfonamide, 5-Chloro-2-methylbenzo[b]thiophene-3-sulfonic acid [4-methoxy-3-(4-methylpiperazin-1-yl)phenyl]amide, Benzofuran-2-sulfonic acid [4-methoxy-3-(4-methylpiperazin-1-yl)phenyl]amide, 1-Methyl-1H-indole-2-sulfonic acid [4-methoxy-3-(4-methylpiperazin-1-yl)phenyl]amide, 5-Chloro-3-methylbenzo[b]thiophene-2-sulfonic acid (4-methoxy-3-piperazin-1-ylphenyl)amide, 5-Chloro-2-methylbenzo[b]thiophene-3-sulfonic acid (4-methoxy-3-piperazin-1-ylphenyl)amide, 1-Methyl-1H-indole-2-sulfonic acid (4-methoxy-3-piperazin-1-ylphenyl)amide, Benzofuran-2-sulfonic acid (4-methoxy-3-piperazin-1-ylphenyl)amide, 5-Chloro-3-methylbenzo[b]thiophene-2-sulphonic acid [3-(4-cyclopropylmethylpiperazin-1-yl)-4-methoxyphenyl]amide, 5-Chloro-3-methylbenzo[b]thiophene-2-sulphonic acid [4-hydroxy-3-(4-methyl-piperazin-1-yl)-phenyl]-amide, 5-Chloro-3-methyl-benzo[b]thiophene-2-sulphonic acid [4-benzyloxy-3-(4-methyl-piperazin-1-yl)-phenyl]-amide, 5-Chloro-3-methylbenzo[b]thiophene-2-sulphonic acid [4-ethoxy-3-(4-methyl-piperazin-1-yl)-phenyl]-amide, 5-Chloro-3-methylbenzo[b]thiophene-2-sulphonic acid [4-isopropoxy-3-(4-methyl-piperazin-1-yl)-phenyl]-amide, 5-Chloro-3-methylbenzo[b]thiophene-2-sulfonic acid [4-chloro-3-(4-methylpiperazin-1-yl)phenyl]amide, 1-5-Chloro-3-methylbenzo[b]thiophene-2-sulfonyl)-6-(4-methylpiperazin-1-yl)-2,3-dihydro-1H-indole, 1-(5-Chloro-3-methylbenzo [b]thiophene-2-sulfonyl)-5-methoxy-6-(4-methylpiperazin-1-yl)-2,3-dihydro-1H-indole, 5-Chloro-3-methylbenzo[b]thiophene-2-sulfonic acid [4-methoxy-2-methyl-3-(4-methylpiperazin-1-yl)phenyl]amide, 5-Chloro-3-methylbenzo[b]thiophene-2-sulfonic acid [2-(2-hydroxyethyl)-4-methoxy-3-(4-methylpiperazin-1-yl)phenyl]amide, 1-(5-Chloro-3-methylbenzo[b]thiophene-2-sulfonyl)-5-methoxy-4-(4-methyl-piperazin-1-yl)-2,3-dihydro-1H-indole hydrochloride, 5-Chloro-3-methylbenzo[b]thiophene-2-sulfonic acid [3-methoxy-4-(4-methyl-piperazin-1-yl)phenyl]amide, 1-(5-Chloro-3-methylbenzo[b]thiophene-2-sulfonyl)-5-phenyl-6-piperazin-1-yl-2,3-dihydro-1H-indole, 5-Chloro-1-(5-chloro-3-methylbenzo[b]thiophene-2-sulfonyl)-6-piperazin-1-yl-2,3-dihydro-1H-indole, 1-(5-Chloro-3-methylbenzo[b]thiophene-2-sulfonyl)-7-piperazin-1-yl-1,2,3,4-tetrahydroquinoline, 5-Chloro-3-methylbenzo[b]thiophene-2-sulfonic acid [4-methyl-3-(4-methylpiperazin-1-yl)phenyl]amide, and pharmaceutically acceptable salts thereof.

10. A compound according to claim 1 which is 5-Chloro-3-methylbenzo[b]thiophene-2-sulfonic acid(4-methoxy-3-piperazin-1-ylphenyl)amide hydrochloride.

11. A pharmaceutical composition which comprises a compound according to claim 1 and a pharmaceutically acceptable carrier or excipient.

12. A method of treating schizophrenia or depression comprising administering a safe and effective amount of a compound according to claim 1.

13. A process for the preparation of a compound of formula (I) or a salt thereof:

$$(R^1)_n\text{—P—A—}\underset{\underset{O}{\|}}{\overset{\overset{O}{\|}}{S}}\text{—N}\underset{R^3}{\overset{R^2}{—}}\text{—Ar}(R^4, R^5) \quad (I)$$

wherein:

P is benzothiophene, benzothiadiazole, quinoline, benzofuran or indole;

R¹ is halogen, C$_{1-6}$alkyl optionally substituted by one or more halogen atoms, C$_{3-6}$cycloalkyl, COC$_{1-6}$alkyl, C$_{1-6}$alkoxy, OCF₃, hydroxy, hydroxyC$_{1-6}$alkyl, hydroxyC$_{1-6}$alkoxy, C$_{1-6}$alkoxyC$_{1-6}$alkoxy, nitro, amino, C$_{1-6}$alkylamino or C$_{1-6}$dialkylamino, cyano or R¹ is phenyl, or naphthyl;

n is 0, 1, 2, 3, 4, 5 or 6:

R² is hydrogen, C$_{1-6}$alkyl or aryl C$_{1-6}$alkyl or R² is linked to R³ to form a group (CH₂)₂ or (CH₂)₃;

R³ is a group R⁵ or together with R⁵ forms a group (CH₂)₂O or (CH₂)₃O or R³ is linked to R² to form a group (CH₂)₂ or (CH₂)₃;

R⁴ is an N-piperazine ring optionally substituted by C$_{1-6}$alkyl; and

R⁵ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, nitro, trifluoromethyl, cyano or aryl, which process comprises the coupling of a compound of formula (II):

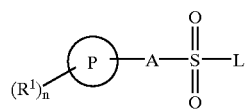 (II)
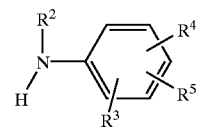 (III)
in which $R^2$, $R^3$, $R^4$ and $R^5$ are as defined in formula (I) or protected derivatives thereof and optionally thereafter:
 removing any protecting groups,
 forming a pharmaceutically acceptable salt.
in which $R^1$, n, P, and A are as defined in formula (I) or protected derivatives thereof and L is a leaving group with a compound of formula (III):
* * * * *